(12) United States Patent
Pantages et al.

(10) Patent No.: US 6,454,717 B1
(45) Date of Patent: Sep. 24, 2002

(54) CONCENTRIC CATHETER DRIVE SHAFT CLUTCH

(75) Inventors: Anthony Pantages, Los Altos; Donald S. Mamayek, Mountain View, both of CA (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/548,564

(22) Filed: Apr. 13, 2000

(51) Int. Cl.$^7$ .................................................. A61B 8/12
(52) U.S. Cl. ........................ 600/466; 604/22; 606/159
(58) Field of Search ........................ 606/159, 169–171; 600/439, 466, 463, 471, 585, 458, 445, 437; 604/99.01, 22; 370/335

(56) References Cited

U.S. PATENT DOCUMENTS

| | | | |
|---|---|---|---|
| 3,838,688 A | 10/1974 | May et al. ................. | 128/214.4 |
| 4,771,774 A | 9/1988 | Simpson ..................... | 128/305 |
| 4,951,677 A | 8/1990 | Crowley et al. ........ | 128/662.06 |
| 4,979,939 A | * 12/1990 | Shiber ......................... | 606/159 |
| 5,002,553 A | 3/1991 | Shiber ......................... | 606/159 |
| 5,554,163 A | 9/1996 | Shturman .................... | 606/159 |
| 5,569,179 A | 10/1996 | Adrian ......................... | 604/22 |
| 5,762,599 A | 6/1998 | Sohn ............................ | 600/30 |
| 5,827,313 A | * 10/1998 | Ream .......................... | 606/171 |
| 5,833,616 A | 11/1998 | Gruner et al. .............. | 600/462 |
| 5,865,178 A | 2/1999 | Yock ........................... | 128/660.03 |
| 5,897,567 A | 4/1999 | Ressemann et al. ......... | 606/159 |
| 5,932,035 A | 8/1999 | Koger et al. ................. | 148/563 |
| 6,027,460 A | * 2/2000 | Shturman .................... | 600/585 |

FOREIGN PATENT DOCUMENTS

| | | | |
|---|---|---|---|
| DE | 39 29 611 | 9/1988 | ............ A61B/8/12 |
| DE | 196 19 774 A1 | 5/1996 | ............ B24B/23/02 |
| EP | 0 163 502 | 12/1985 | ............ A61B/17/22 |
| EP | 0 397 459 | 11/1990 | ............ A61M/25/01 |
| EP | 0397459 | 11/1990 | |
| JP | 10-66696 | 3/1998 | ............ A61B/8/12 |
| WO | WO 92/16147 | 10/1992 | ............ A61B/8/14 |

\* cited by examiner

Primary Examiner—Marvin M. Lateef
Assistant Examiner—Ruby Jain
(74) Attorney, Agent, or Firm—Lyon & Lyon LLP

(57) ABSTRACT

Rotating element catheters and catheter assemblies employ clutch assemblies for preventing rotational energy from being transmitted from a motor drive unit to the catheter element under defined circumstances. The catheter assembly includes an elongate member in which there is disposed a rotatable catheter drive cable. The catheter drive cable may have an operative element, e.g., an ultrasonic transducer or an artherectomy blade, distally mounted thereon for providing diagnostic or therapeutic functions to the physician. To control the rotation of the catheter drive shaft, the clutch assembly is configured such that the catheter drive shaft is operated in a drive mode (i.e., it is allowed to rotate) and in a release mode (i.e., it is prevented from rotating). The clutch assembly includes a driver member comprising a first cylindrical body, and a driven member comprising a second cylindrical body in a concentric relationship with the first cylindrical body. The first cylindrical body can be a rigid cylindrical member, and the second cylindrical body can be a compliant tube interference fit about the cylindrical member. Or the first cylindrical body can be a receptacle with cutouts, and the second cylindrical body can be a cylindrical member disposed within the receptacle, with the surface of the cylindrical member being exposed through the cutouts. A spring clamp can then be interference fitted over the receptacle and exposed arcuate surfaces of the cylindrical member.

23 Claims, 11 Drawing Sheets

CONCENTRIC CATHETER DRIVE SHAFT CLUTCH

RELATED APPLICATION

This application is related to application Ser. No. 09/548,860, application Ser. No. 09/548,690, and application Ser. No. 09/548,692, all filed concurrently herewith and all expressly incorporated herein by reference.

FIELD OF THE INVENTION

This invention relates generally to catheters, and more particularly to catheters having rotatable operative elements.

BACKGROUND

Currently, there exist rotating element catheters, which can be used by physicians to provide a diagnostic or therapeutic effect within the body tissue of a patient, e.g., ultrasonic imaging or artherectomy. A typical rotating element catheter includes a flexible drive cable that extends the length of the catheter body, terminating proximally in a motor drive unit. An operative element, e.g., an ultrasonic transducer or artherectomy blade, is distally mounted to the drive cable. Operation of the drive unit rotates the drive cable, which, in turn, rotates the operative element at high speeds to produce the desired diagnostic or therapeutic effect. Due to the nature of placing indiscriminately rotating elements inside a patient, there is always a risk that the rotating element could inadvertently damage tissue if the catheter is defective or mishandled.

For example, some ultrasonic imaging catheters can provide two-dimensional 360° images along the length of a blood vessel by rotating an ultrasonic transducer at high speeds, while linearly moving the ultrasonic transducer in the distal direction relative to the catheter member. If the distal end of the catheter member is kinked, or otherwise formed into a tight curve, there exists the possibility, however so slight, that the rotating ultrasonic transducer could perforate through the catheter member and damage the surrounding tissue. This is caused, in part, by the fact that the drive unit is designed to maintain the speed of the transducer at a set level, accordingly increasing or decreasing the torque that is applied to the drive cable. In doing so, the drive unit does not discriminate between normal frictional loads, i.e., frictional loads caused by normal friction between the drive cable and catheter member, and abnormal friction loads, i.e., frictional loads caused by an abnormal circumstance, e.g., the boring of the transducer through the wall of the catheter member.

As a precaution, these types of ultrasonic imaging catheters are designed, such that the drive shaft fails if the torque required to rotate the ultrasonic transducer becomes too great. This design contemplates providing a circumferential space between the drive cable and the catheter member along a portion of the catheter, allowing the drive cable to wind or ball up within the space when the torque applied to the drive cable exceeds a critical magnitude. Presumably, such an excess in force will occur if the rotating ultrasonic transducer begins to perforate the catheter member, resulting in a failed drive cable, and preventing the ultrasonic transducer from further boring through the catheter member.

Typically, however, the drive shaft fails, not because the ultrasonic transducer is boring through the catheter member, but rather because the drive cable is subjected to excessive frictional forces. Such forces are often a result of having to route the catheter through the tortuous vasculature of a patient, forcing the drive cable to rotate through many curves. Any mishandling of the catheter while operating the motor drive unit, e.g., overtightening the touhy-borst valve through which the catheter is introduced into the patient, exacerbates this situation. Because the drive unit is designed to maintain the rotation of the ultrasonic transducer at a uniform speed, the motor drive unit increases the torque that is applied to the drive cable to compensate for any increase in frictional force, thereby risking failure of the drive cable. In fact, of all the failed ultrasonic imaging catheters returned to the assignee of this application, approximately seventy percent fail as a result of this phenomenon.

There thus remains a need to prevent premature failure of a drive cable within a catheter, while minimizing the potential risk of inadvertently damaging tissue by the rotating operative element distally mounted on the drive cable.

SUMMARY OF THE INVENTION

The present inventions are broadly directed to rotating element catheters and catheter assemblies that employ concentric members to prevent rotational energy from being transmitted from a motor drive unit to the catheter element under defined circumstances.

In accordance with a first aspect of the present inventions, a catheter assembly includes an elongate member in which there is disposed a rotatable catheter drive shaft, e.g., a flexible drive cable. The catheter drive shaft may have an operative element, e.g., an ultrasonic transducer or an artherectomy blade, distally mounted thereon for providing diagnostic or therapeutic functions to the physician. In the case of ultrasonic imaging, the elongate member can take the form of a telescoping guide sheath slidably disposed about an imaging core (i.e., the catheter drive shaft and ultrasonic transducer) to provide the physician with two-dimensional 360° ultrasonic images of surrounding body tissue.

To control the rotation of the catheter drive shaft, the catheter assembly includes a driver member comprising a first cylindrical body, and a driven member comprising a second cylindrical body in a concentric relationship with the first cylindrical member. The driven member is rotatably coupled (either directly or indirectly) to the proximal end of the catheter drive shaft. The first cylindrical body cooperates with the second cylindrical body, e.g., frictionally or magnetically, such that the driven and driver members are rotatably engaged with each other before the applied torque exceeds a critical magnitude, and rotatably disengaged with each other after the applied torque exceeds the critical magnitude. The driven and driver members are preferably located entirely within the catheter, e.g., in a proximal hub configured to interface with a motor drive unit, but a portion of the entirety of the driven and driver members can be located elsewhere, e.g., in the motor drive unit.

In accordance with a second aspect of the present inventions, one end of a compliant tube composed of a material, such as rubber or silicone, is interference fitted over a rigid cylindrical member. One of a driven member and a driver member includes the compliant tube, and the other of the driven member and driver member includes the rigid cylindrical member. In the preferred embodiment, the member that includes the compliant tube comprises another rigid cylindrical member over which the other end of the compliant tube is affixed by suitable means, e.g., bonding.

In accordance with a third aspect of the present inventions, a cylindrical member is disposed within the cylindrical cavity of a receptacle, wherein the receptacle includes one or more cutouts to expose one or more arcuate surfaces of the cylindrical member. One of a driven member and a driver member includes the cylindrical member, and the other of the driven member and driver member includes the receptacle. A spring clamp is interference fit around the receptacle and the exposed arcuate surfaces of the cylindrical member.

Other and further objects, features, aspects, and advantages of the present invention will become better understood with the following detailed description of the accompanying drawings.

BRIEF DESCRIPTION OF THE DRAWINGS

The drawings illustrate both the design and utility of preferred embodiments of the present invention, in which.

DETAILED DESCRIPTION OF THE PREFERRED EMBODIMENTS

Figure 1:
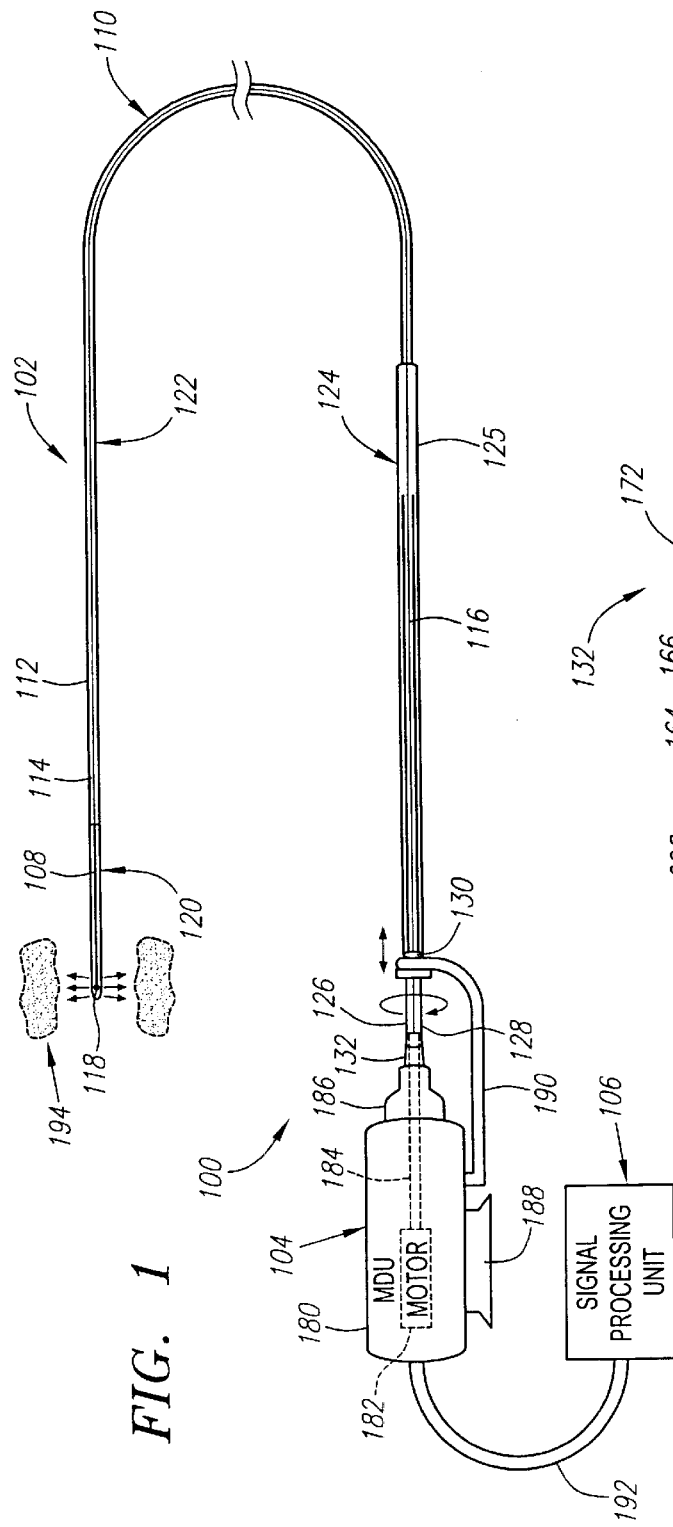
FIG. 1 is a schematic view of an ultrasonic imaging system constructed in accordance with the present inventions.

Referring to FIG. 1, an exemplary ultrasound imaging catheter system 100, constructed in accordance with the present invention, is provided for ultrasonically imaging a patient's internal body tissue 194, e.g., the wall of an artery. The catheter system 100 generally includes a flexible ultrasonic imaging catheter 102, which houses an ultrasonic imaging core 108, a motor drive unit 104 (MDU) for providing a source of rotational energy to the imaging core 108, and an ultrasonic signal processing unit 106 operatively connected to the imaging core 108 for providing an ultrasonic image of the targeted tissue to a physician.

The catheter 102 includes an elongate telescoping catheter body 110, which facilitates the rotational and longitudinal translation of the imaging core 108. In particular, the catheter body 110 includes an outer guide sheath 112 with an imaging lumen 114. The imaging core 108 is disposed within the imaging lumen 114, allowing the imaging core 108 to be rotationally and longitudinally translated with respect to the guide sheath 112.

The imaging core 108 comprises a flexible catheter drive shaft 110, i.e., a drive cable, with an ultrasonic transducer 118 distally mounted thereon. As is well known in the art, the transducer 118 is composed of a layer of piezoelectrical material, with acoustic matching and backing layers suitably formed on the opposite sides thereof (not individually shown). The drive cable 116 is preferably designed, such that it possesses a high torsional stiffness and a low bending stiffness. For example, the drive cable 116 can be made of two counterwound layers of multifilar coils that are fabricated using techniques disclosed in Crowley et al., U.S. Pat. No. 4,951,677, the disclosure of which is fully and expressly incorporated herein by reference. Thus, the transducer 118 rotates about a longitudinal axis in response to the application of a torque on the proximal end of the drive cable 116. The imaging core 108 further includes signal wires 114 (shown in FIG. 2), which are suitably connected to the transducer 118 by suitable means, e.g., welding. The signal wires 114 are routed through the drive cable 116 from the transducer 118, extending out the proximal end of the drive cable 116.

The outer guide sheath 112 can be generally divided into three sections: an acoustic window 120, a main section 122, and an telescoping section 124. The acoustic window 120 houses the transducer 118, and when filled with a suitable imaging solution, allows ultrasonic energy UE to be transmitted between the transducer 118 and the surrounding body tissue. The proximal end of the acoustic window 120 is suitably bonded to the distal end of the main section 122, which extends almost the entire length of the guide sheath 112. The main section 122 is characterized by a relatively stiff structure, which not only facilitates advancement of the catheter body 110 through the tortuous vasculature of the patient, but also facilitates advancement of the imaging core 108 through the imaging lumen 114. The distal end of the telescoping section 124 is suitably bonded to the proximal end of the main section 122, and includes a semi-rigid tube 125 through which a smaller diameter semi-rigid tube 126 is slidably disposed. The semi-rigid tube 126 extends proximally from the telescoping section 124 and serves to provide rigidity to the drive cable 116 outside of the guide sheath 112.

In this regard, the semi-rigid tube 126 includes a lumen 128 through which the proximal end of the drive cable 116 extends. Although the drive cable 116 rotates relative to the semi-rigid tube 126, as will be described in further detail below, the drive cable 116 and semi-rigid tube 126 are longitudinally affixed with respect to each other. Thus, relative translation of the semi-rigid tube 126 in the distal direction necessarily translates the imaging core 108 in the distal direction with respect to the guide sheath 112. Similarly, relative translation of the semi-rigid tube 126 in the proximal direction necessarily translates the imaging core 108 in the proximal direction with respect to the guide sheath 112. To facilitate the telescoping action of the catheter 102, the telescoping section 124 includes an anchor housing 130 for connection to a rigid pullback arm 190 of the MDU 104, as will be described in further detail below.

The catheter 102 further includes a proximal hub 132, which mates with a hub 186 of the MDU 104. The catheter hub 132 provides the necessary mechanical interface between the imaging core 108 and the MDU 104, as well as the electrical interface between the imaging core 108 and the signal processing unit 106. In the illustrated embodiment, the catheter hub 132 is configured as a male adapter, with the MDU hub 186 being configured as a female adapter.

Figure 2:
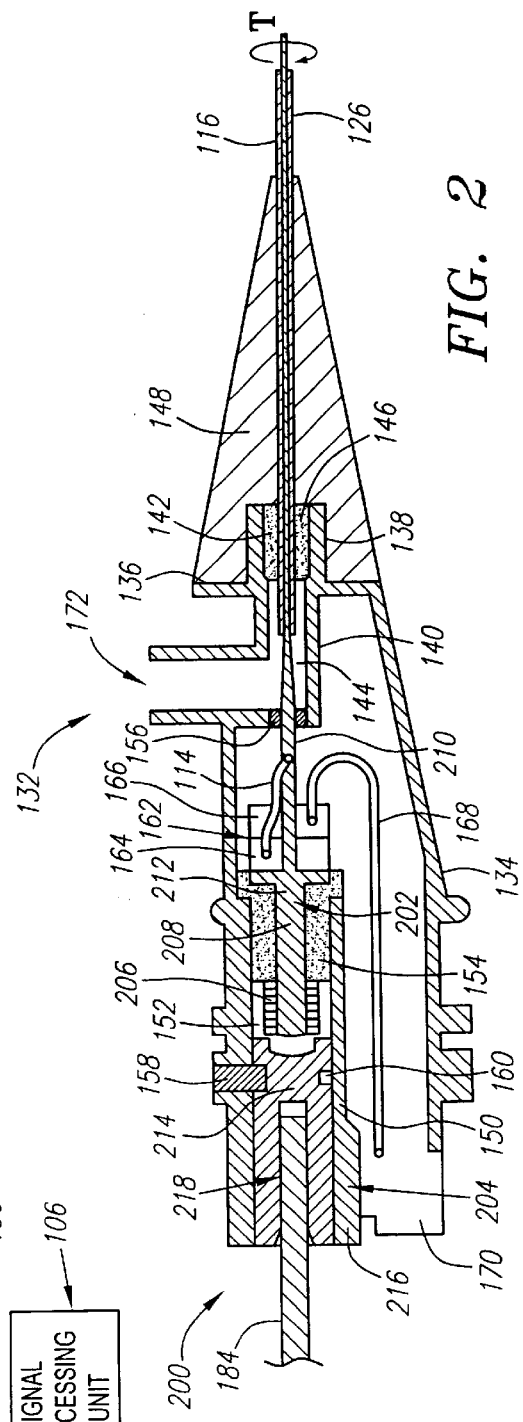
FIG. 2 is a longitudinal section of a first preferred embodiment of an automatic clutch assembly employed in the system of FIG. 1.

Referring specifically to FIG. 2, the catheter hub 132 includes a rigid housing 134 composed of a suitable material, e.g., plastic, and is molded in a shape that facilitates firm seating of the catheter hub 132 within the MDU hub 186. The housing 134 further includes a pair of spring clamps (not shown), which interact with the MDU hub 186 to removably affix the catheter hub 132 therein.

The proximal end of the housing 134 includes a transverse wall 136 from which opposing distally and proximally extending cylindrical walls 138 and 140 extend. The cylindrical walls 138 and 140 respectively include cavities 142 and 144, which are in communication with each other through the transverse wall 136. The semi-rigid tube 126 is permanently fixed within the distal cylindrical wall cavity 142 using adhesive 146. In this regard, the semi-rigid tube 126 is affixed to and extends through the adhesive 146, across the transverse wall 136, and into the proximal cylindrical wall cavity 144. A flexible rubber grommet 148 is suitably mounted to the distal end of the housing 134, around the distal cylindrical wall 138 and abutting the distal face of the transverse wall 136. The grommet 148 receives and provides stress relief for the drive cable 116 and semi-rigid tube 126.

The catheter hub 132 further includes an automatic clutch assembly 200, which is firmly and rotatably seated within a cavity 152 of an inner cylindrical wall 150 formed within the housing 134. The cylindrical wall 150 is an axial alignment with the distal and proximal cylindrical walls 138 and 140, and thus, the clutch assembly 200 is in axial alignment with the drive cable 116. The clutch assembly 200 is configured to advantageously operate the drive cable 116 in either a drive mode or a release mode. Specifically, when a torque T is applied to the proximal end of the drive cable 116, the clutch assembly 200 provides a means for permitting rotation of the drive cable 116 before the applied torque T exceeds a critical magnitude (drive mode), and provides a means for preventing rotation of the drive cable 116 after the applied torque T exceeds the critical magnitude (release mode).

To this end, the clutch assembly 200 comprises a driven member 202 and a driver member 204, which, as will be described in further detail below, interact with each other to provide the aforementioned clutching function. The driven member 202 comprises a generally cylindrical rigid member 208, which is composed of a suitable rigid material, e.g., stainless steel. The cylindrical member 208 includes an elongate shaft 210 with a proximally facing boss 212. The boss 212 and the shaft 210 can be molded as an integral unit, or can alternatively be affixed to each other using suitable means, e.g., welding.

The driven member 202 is rotatably coupled to the drive cable 118. Specifically, the driven member 202 is held in axial alignment with the drive cable 118 by a bushing 154, which is composed of a suitably rigid bearing material, e.g., bronze. The bushing 154 is suitably bonded within the cavity 152 of the cylindrical wall 150, with the boss 212 of the driven member 202 being rotatably disposed with the bushing 154. Likewise, a seal 156 is suitably bonded within the cavity 144 of the cylindrical wall 140, with the shaft 210 being rotatably disposed within the seal 156. The driven member 202 is rotatably engaged with the drive cable 116 by suitably mounting the distal end of the shaft 210 to the proximal end of the drive cable 116, e.g., by welding. It is noted that a portion of the shaft 210 is hollow, which allows the signal wires 114 from the drive cable 116 to extend therethrough.

The driver member 204 comprises a generally cylindrical rigid member 214, which is molded from a suitably rigid material, e.g., plastic. The cylindrical member 214 includes a proximally facing receptacle 216 with a cavity 218 formed therein for receiving the distal end of a rigid motor drive shaft 184 from the MDU 104 (shown in FIG. 1), when the catheter hub 132 is mated with the MDU hub 186. To facilitate proper and firm engagement with the motor drive shaft 184, the receptacle 216 and motor drive shaft 184 are keyed, such that the receptacle 216 rotatably engages the motor drive shaft 184 when inserted into the cavity 218. The driver member 204 is held in longitudinal abeyance by a rigid arcuate member 158, which is mounted through the housing 134 and engages an annular recess 160 formed in the cylindrical member 214.

The driver member 204 further includes a coil spring 206, which integrally rotates with and is affixed to the cylindrical member 214. As will be discussed in further detail below, the coil spring 206 interacts with the cylindrical rigid member 208 of the driven member 202 in a manner that actuates the clutching action between the driven member 202 and the driver member 204.

The catheter hub 132 further includes an inductive coupler 162, which is firmly seated within the housing 134 in an axial relationship with the clutch assembly 200. The inductive coupler 162 provides the means for inductively coupling the electrical energy from the signal wires 114, which rotate by virtue of their association with the rotating drive cable 116, and a stationary platform, i.e., the signal processing unit 106. To this end, the inductive coupler 162 includes a disk-shaped magnetic rotor 164 and a disk-shaped magnetic stator 166, which are located adjacent each other in a coaxial manner. The shaft 210 of the driven member 202 extends entirely through the inductive coupler 162, where it is rotatably engaged with the rotor 164. Thus, the rotor 164 of the inductive coupler 162 integrally rotates with the driven member 202. The signal wires 114 extend from a transverse hole (not shown) made in the shaft 210, and are suitably connected to the rotor 164. Lead-in signal wires 168 are mounted between the stator 166 and an electrical jack 170 mounted on the housing 134. In this manner, electrical signals can be transmitted between the electrical jack 170 and the signal wires 114 within the drive cable 116 when the imaging core 108 is rotating.

The catheter hub 132 further includes an infusion port 172 formed from the housing 134, which is in fluid communication with the cavity 144 of the distal cylindrical wall 140. Because the lumen 128 of the semi-rigid tube 126 (shown in FIG. 1) is in fluid communication with the cavity 144, the infusion port 172 is in fluid communication with the imaging lumen 114 of the guide sheath 112. Thus, the acoustic window 120 can be filled with a suitable imaging fluid, e.g., a saline solution, introduced through the infusion port 172.

Referring back to FIG. 1, the MDU 104 provides the means for rotationally and longitudinally translating the imaging core 108 with respect to the guide sheath 112. In particular, the MDU 104 comprises a casing 180 in which there is firmly affixed a motor 182 and the aforementioned motor drive shaft 184 (motor and shaft shown in phantom). As briefly discussed above, the MDU hub 186 mates with the proximal catheter hub 132, with the distal end of the motor drive shaft 184 being rotatably engaged with the driver member 204 of the clutch assembly 200. The casing 180 is mounted to a carriage 188 and is in a sliding relationship therewith. A drive train (not shown) is coupled between the casing 180 and the motor 182, and is configured to longitudinally translate the casing 180 with respect to the carriage 188 in a controlled manner when engaged with the motor 182.

Further details regarding the use of a single motor to actuate both rotation of a drive shaft and longitudinal translation of a drive unit casing are disclosed in U.S. Pat. No. 6,004,271, the disclosure of which is fully and expressly incorporated herein by reference. Alternatively, separate and distinct motors can be used to respectively actuate rotation of the motor drive shaft 184 and longitudinal movement of the casing 180. Further details regarding the use of two motors to respectively actuate rotation of a drive shaft and longitudinal translation of a drive unit casing are disclosed in U.S. Pat. No. 6,013,030, the disclosure of which is fully and expressly incorporated herein by reference.

The MDU 104 further includes a rigid pull back arm 190, one end of which is mounted to the anchor housing 130 of the guide sheath 112, and the other end of which is mounted to the carriage 188. In this manner, when the MDU 104 is operated, the rotating imaging core 108 longitudinally translates in relation to the guide sheath 112, since the imaging core 108 is longitudinally engaged with the casing 180 via the catheter hub 132, and the guide sheath 112 is fixed in place by the pullback arm 190.

The MDU 104 includes feedback circuitry with an encoder (not shown), which senses the loss of rotational speed in the presence of an increased friction force between the imaging core 108 and the catheter body. In response, the feedback circuitry increases the current delivered to motor 182, maintaining the motor drive shaft 184 at the set speed. This increased current translates to an increased torque T applied to the proximal end of the drive cable 116.

The signal processing unit 106 generally comprises a controller, data interpretation unit, monitor, keyboard, etc. (not individually shown). The signal processing unit 106 is electrically coupled to the transducer 118 of the imaging core 108 through the MDU 104. Specifically, a power/data cable 192 transmits input/output data between the MDU 104 and signal processing unit 106, while providing DC electrical power to the MDU 104. Upon mating of the catheter hub 132 with the MDU hub 186, the MDU 104 is, in turn, electrically coupled to the imaging core 108 via signal wires 114 connected to the electrical jack 170 (shown in FIG. 2).

During operation, the signal processing unit 106 transmits electrical signals to the transducer 118 via the aforedescribed electrical path. In response, the transducer 118 is electrically excited, emitting ultrasonic energy UE through the acoustic window 120 into the surrounding body tissue. The ultrasonic energy UE is reflected from the surrounding body tissue, back through the acoustic window 120, and into the transducer 118. The ultrasonic excited transducer 118, in turn, emits electrical signals, which are transmitted back to the signal processing unit 106 via the electrical path. By virtue of the fact that the transducer 118 is being simultaneously rotated and longitudinally translated during this process, the received electrical signals represent a multitude of 360° data slices, which are constructed by the signal processing unit 106 into a two-dimensional image of the body tissue.

As stated above, the MDU 104 attempts to maintain the speed of the motor drive shaft 184 at a set speed, by increasing or decreasing the torque applied to the motor drive shaft 184 in response to a variable frictional load. The clutch assembly 200, however, provides a check on the MDU 104. In the presence of normal frictional loads, the clutch assembly 200 automatically engages the motor drive shaft 184 with the drive cable 116, in which case, the drive cable 116 rotates with the motor drive shaft 184 (drive mode). In the presence of abnormal frictional loads, however, the clutch assembly 200 automatically disengages the motor drive shaft 184 from the drive cable 116, in which case the drive cable 116 does not rotate with the motor drive shaft 184 (release mode).

Figure 3:
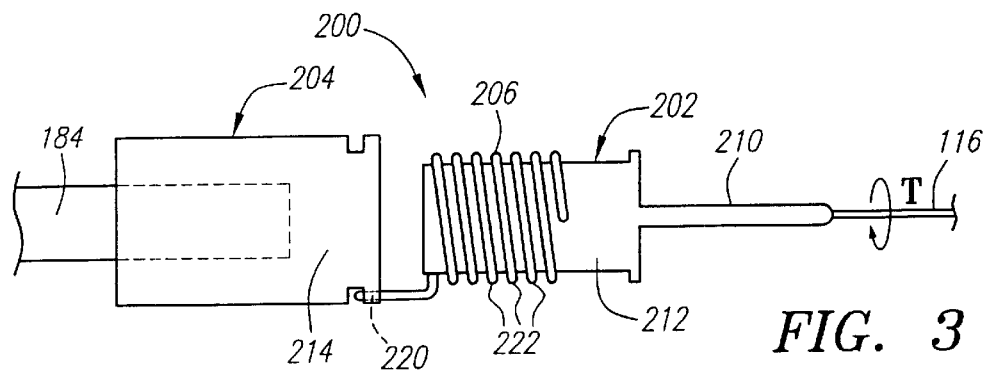
FIG. 3 is a side view of the clutch assembly of FIG. 2.

Referring to FIG. 3, the motor drive shaft 184 (shown partially in phantom) is shown applying the torque T to the proximal end of the drive cable 116 (via the clutch assembly 200) in a clockwise direction. As noted above, the current magnitude of the applied torque T at any given time depends on the frictional load. Taking the current magnitude of the applied torque T into account, the clutch assembly 200 allows the drive cable 116 to be alternately operated between the drive mode and the release mode. To this end, the driven member 202 and the driver member 204 are conditionally affixed to each other. That is, the driven member 202 is rotatably engaged with the driver member 204 before the current magnitude of the applied torque T exceeds the critical magnitude, and is rotatably disengaged with the driver member 204 after the current magnitude of the applied torque T exceeds the critical magnitude.

Figure 4:
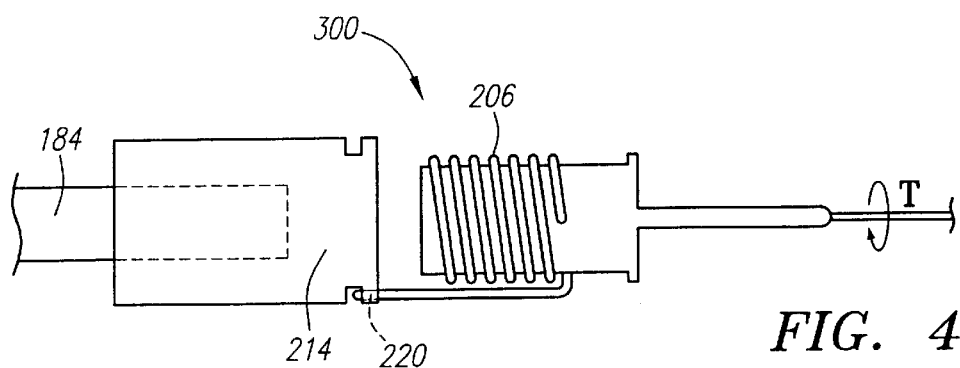
FIG. 4 is a side view of a second preferred embodiment of an automatic clutch assembly employed in the imaging system of FIG. 1.

In particular, the coil spring 206 is affixed to the cylindrical member 214 of the driver member 204 by bending the proximal end of the coil spring 206 into engagement with a hole 220 formed in the cylindrical member 214. Alternatively, the coil spring 206 can be affixed to the cylindrical member 214 by bending the distal end of the coil spring 206 into engagement with the hole 220, as shown in the automatic clutch assembly 300 depicted in FIG. 4.

Referring back to FIG. 3, the coil spring 206 provides the means for effecting the aforementioned clutching action. Specifically, the body of the coil spring 206, which, in the illustrated embodiment, is represented by seven and one-half coils 222, is interference fitted over the boss 212, such that a frictionally engaging relationship is formed therebetween. In this regard, the normal inner diameter (the inner diameter in the absence of an external force) of the coil spring 206 is slightly less than the outer diameter of the boss 212. Preferably, the outer surface of the driven member 202 is polished to a substantially uniform diameter to provide a substantially uniform contact between the coil spring 206 and boss 212.

The coil spring 206 is preferably wound in a direction, such that it tends to "unwind" in the presence of the applied torque T. That is, the interference fit between the coil spring 206 and the boss 212 decreases as the applied torque T increases. Thus, if the proximal end of the coil spring 206 is affixed to the cylindrical member 214 of the driver member 204 (as shown in FIG. 2), the coil spring 206 is wound in the counterclockwise direction from the proximal end. In contrast, if the distal end of the coil spring 206 is affixed to the cylindrical member 214 of the driver member 204 (as shown in FIG. 3), the coil spring 206 is wound in the clockwise direction from the proximal end.

By way of nonlimiting example, the outer and inner diameters of the coil spring 206 can be 0.160 and 0.124 inches, with the diameter of the wire being 0.018 inches. Assuming an exemplary interference fit between the coil spring 206 and driven member 202 of between 0.001 and 0.002 inches (in the absence of an applied torque), the outer diameter of the boss 212 is preferably between 0.122 and 0.123 inches.

Figure 5:
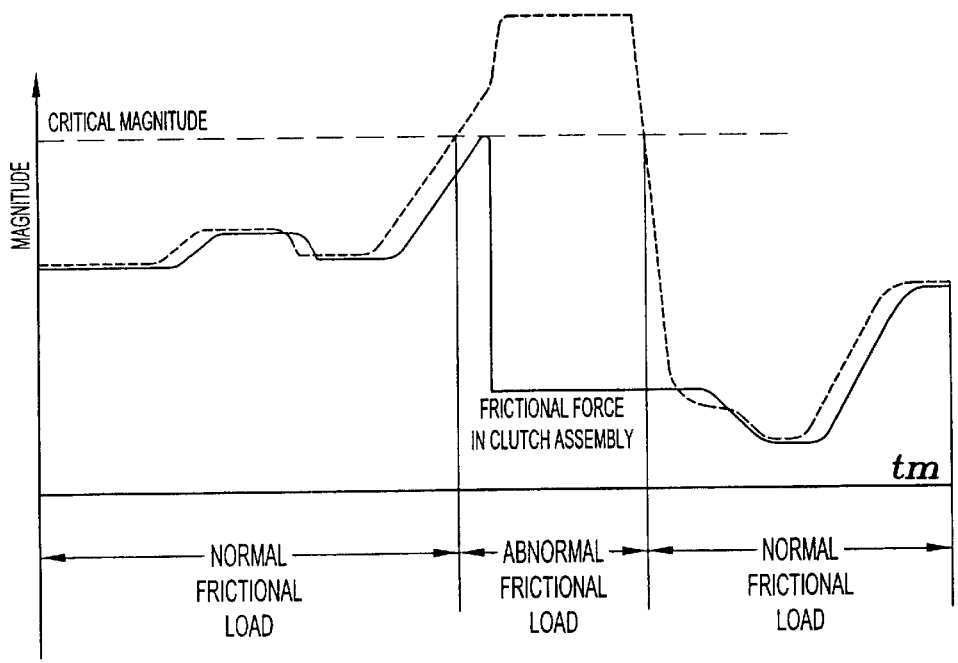
FIG. 5 is a diagram showing the magnitude of a torque applied to a catheter drive shaft within the imaging system over a time period in response to a varying frictional load of the catheter drive shaft.

The operation of the clutch assembly 200 will now be described. FIG. 5 specifically depicts the magnitude of the applied torque T (solid line) and the magnitude of a representative frictional load variance in the drive cable 116 (dashed line) over time. FIG. 5 also indicates the particular mode in which the drive cable 116 is operated, assuming that the drive cable 116 is initially operated in the drive mode. Note that the magnitude of the applied torque T tracks the magnitude of the frictional load, which results from the tendency of the MDU 104 to maintain the motor drive shaft 184 at a uniform speed. The lag between the magnitude of the applied torque T and the magnitude of the frictional load represents the time taken for the MDU 104 to adjust the magnitude of the applied torque T in response to the change in the magnitude of the frictional load.

As can be seen from FIG. 5, as long as the frictional load remains normal, the current magnitude of the applied torque T remains below the critical magnitude. Thus, operation of the drive cable 116 is maintained in the drive mode. Specifically, as long as the critical magnitude is not exceeded, the current magnitude of the applied torque T does not overcome the frictional force generated by the interference fit between the coil spring 206 and the boss 212 (in spite of the reduced interference fit due to the "unwinding" of the coil spring 206 in the presence of the applied torque T). Thus, the driven member 202 remains rotatably engaged with the driver member 204. As a result, the drive cable 116 is rotatably coupled to, and integrally rotates with, the motor drive shaft 184. That is, the drive cable 116 is operated in the drive mode.

As can be seen from FIG. 5, once the frictional load becomes abnormal, the drive cable 116 is operated in the release mode. Specifically, once the critical magnitude is exceeded, the current magnitude of the applied torque T overcomes the frictional force generated by the interference fit between the coil spring 206 and the boss 212 (facilitated by the decrease in the interference fit due to the "winding" of the coil spring 206 in the presence of the applied torque T). Thus, the driven member 202 becomes rotatably disengaged with the driver member 204. As a result, the drive cable 116 is rotatably uncoupled from, and does not integrally rotate with, the motor drive shaft 184. That is, the drive cable 116 is operated in the release mode.

As can be seen from FIG. 5, once the drive cable 116 is operated in the release mode, the current magnitude of the applied torque T drops to a level well below the critical magnitude. At this point, the current magnitude of the applied torque T tracks the magnitude of the frictional force between the rotatably disengaged coil spring 206 and boss 212, which generally remains uniform. The substantial drop in the current magnitude of the applied torque T is due to the frictional changes in the clutch assembly 200. Specifically, the transition from a rotatably engaged relationship to a rotatably disengaged relationship (i.e., transition from drive mode to release mode) is determined by a frictional force between the coil spring 206 and boss 212 that is based upon a stationary coefficient of friction. Once this transition is made, the frictional force between the coil spring 206 and the boss 212 is based upon a dynamic coefficient of friction, which, as is well known, is less than the stationary coefficient of friction. The reduced frictional force translates to a reduced applied torque needed to maintain the motor drive shaft 184 at a uniform set speed.

As long as the MDU 104 maintains rotation of the motor drive shaft 184, once the drive cable 116 is operated in the release mode, operation of the drive cable 116 does not return to the drive mode until the frictional load of the drive cable 116 drops below the frictional force between the disengaged coil spring 206 and boss 212. It can thus be said that the clutch assembly 200 has a built-in hysteresis, ensuring that the drive cable 116 will not be operated in the drive mode until the frictional load is well within the normal range, e.g., by retracting the catheter or loosening the touhy-borst valve. Once this occurs, operation of the drive cable 116 returns to the drive mode, and the current magnitude of the applied torque T again tracks the magnitude of the frictional load. It should be noted that the imaging core 108 can be repeatedly cycled between the drive mode and release mode without wearing out the clutch assembly 200 due to the intrinsic ability of the coil spring 206 to consistently return to its normal diameter.

Figure 6:
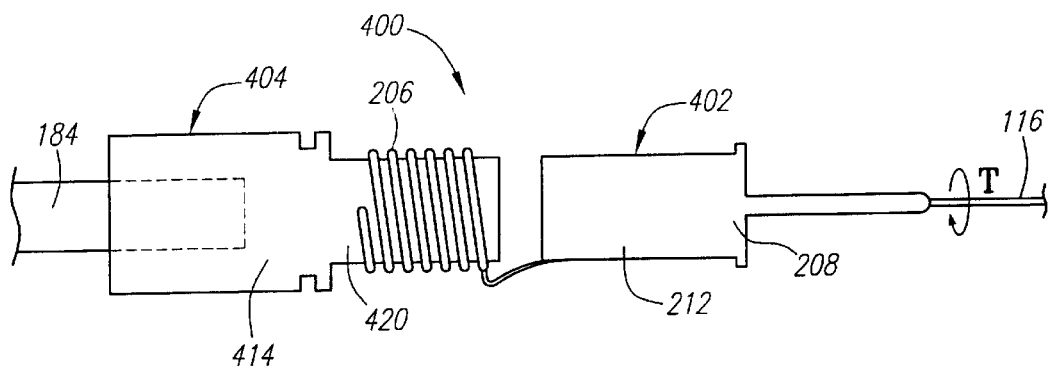
FIG. 6 is a side view of a third preferred embodiment of an automatic clutch assembly employed in the imaging system of FIG. 1.

FIG. 6 depicts an alternative embodiment of an automatic clutch assembly 400, which is constructed in accordance with the present inventions. Like the clutch assembly 200 described above, the clutch assembly 400 includes a driven member 402 and a driver member 404 that are conditionally affixed to each other, wherein the clutching function of the clutch assembly 400 is frictionally actuated by the coil spring 206. The clutch assembly 400 differs from the clutch assembly 200, however, in that the driven member 402, rather than the driver member 404, includes the coil spring 206.

Specifically, the driven member 402 is similar to the above-described driven member 202 (see FIG. 3), with the exception that it includes the coil spring 206, which is affixed to the cylindrical member 208 by bending the distal end of the coil spring 206 into engagement with the boss 212 by suitable means, e.g., welding. Alternatively, the coil spring 206 can be affixed to the cylindrical member 208 by bending the proximal end of the coil spring 206 into engagement with the boss 212, as shown in the automatic clutch assembly 500 depicted in FIG. 7.

Figure 7:
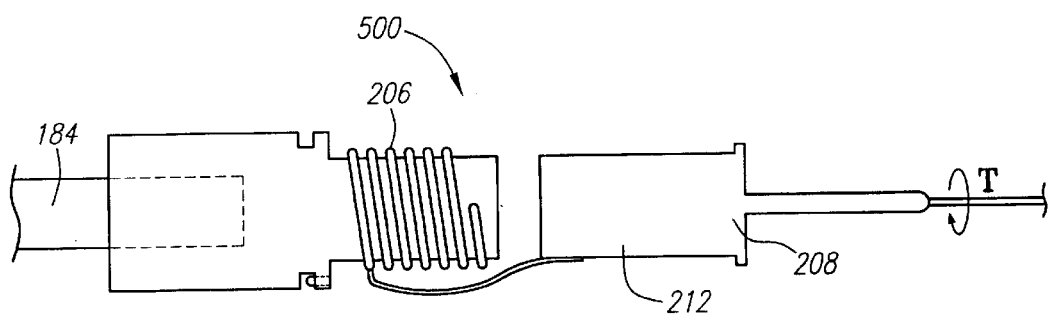
FIG. 7 is a side view of a fourth preferred embodiment of an automatic clutch assembly employed in the imaging system of FIG. 1.

Referring back to FIG. 6, the driver member 404 includes a generally cylindrical rigid member 414, which is constructed similarly to the above-described cylindrical member 214 (see FIG. 3), with the exception that the cylindrical member 414 includes a distally facing transitional shaft 420. The body of the coil spring 206 is interference fit about the transitional shaft 420 in the same manner as that described above with respect to the coil spring 206 and boss 212 (see FIG. 3). Again, the coil spring 206 is preferably wound in a direction, such that it tends to "unwind" in the presence of the applied torque T. Thus, if the distal end of the coil spring 206 is affixed to the boss 212 (as shown in FIG. 6), the coil spring 206 is wound in the clockwise direction from the proximal end. In contrast, if the proximal end of the coil spring 206 is affixed to the boss 212 (as shown in FIG. 7), the coil spring 206 is wound in the counterclockwise direction from the proximal end.

The operation of the clutch assembly 400 is identical to that of the clutch assembly 200, with the exception that the coil spring 206 frictionally interacts with the transitional shaft 420 of the driver member 404, rather than the boss 212 of the driven member 202.

Figure 8:
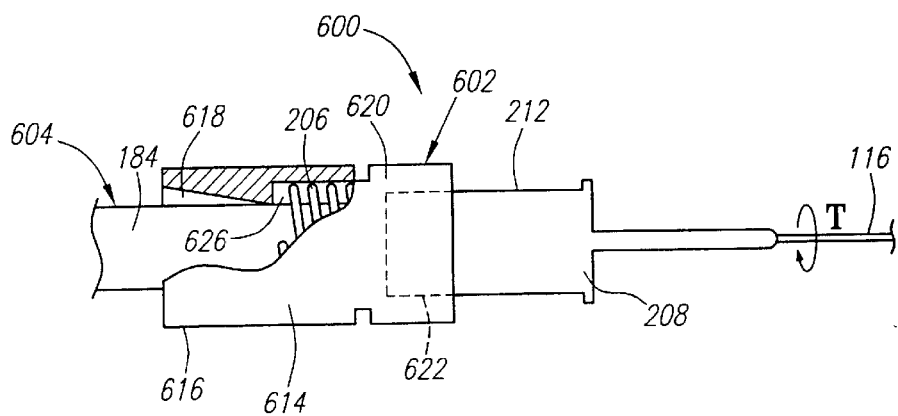
FIG. 8 is a partially cut-away side view of a fifth preferred embodiment of an automatic clutch assembly employed in the imaging system of FIG. 1.

FIG. 8 depicts another alternative embodiment of an automatic clutch assembly 600, which is constructed in accordance with the present invention. Like the clutch assembly 200 described above, the clutch assembly 600 includes a driven member 602 and a driver member 604 that are conditionally affixed to each other. The clutch assembly 600 differs from the clutch assembly 200, however, in that the driver member 604 resides in the MDU 104, rather than in the catheter hub 132 (shown in FIG. 1).

Specifically, the driver member 604 comprises the motor drive shaft 184 itself. The driven member 602 includes the above-described cylindrical member 208 (see FIG. 3), as well as a generally cylindrical rigid member 614, which is molded from a suitably rigid material, e.g., plastic. The cylindrical member 614 includes a distally facing receptacle 620 with a cavity 622 formed therein, wherein the boss 212 (shown partially in phantom) of the cylindrical member 208 is mounted by suitable means, e.g., bonding. Like the above-described cylindrical member 214 (see FIG. 3), the cylindrical member 614 further includes a proximally facing receptacle 616 with a cavity 618 formed therein for receiving the distal end of a rigid motor drive shaft 184 from the MDU 104 (shown in FIG. 2), when the catheter hub 132 is mated with the MDU hub 186. The receptacle 616 and motor drive shaft 184, however, are not keyed, such that the motor drive shaft 184 freely rotates with the cavity 618 absent restraint.

The driven member 602 further includes the coil spring 206, which is seated within an annular recess 626 formed within the cavity 618, with the distal end of the coil spring 206 being suitably mounted to the receptacle 616 distally adjacent the cavity 618. The diameter of the annular recess 626 is slightly greater than the normal outer diameter of the coil spring 206, whereby expansion of the coil spring 206 is allowed, i.e., the coil spring 206 is allowed to "unwind." The normal inner diameter of the coil spring 206 is slightly smaller than the outer diameter of the distal end of the motor drive shaft 184, such that the coil spring 206 can be interference fitted over the distal end of the motor drive shaft 184. Again, the coil spring 206 is preferably wound in a direction, such that it tends to "unwind" in the presence of the applied torque T. In the illustrated embodiment, the coil spring 206 is wound in the clockwise direction from the proximal end. As can be seen, the cavity 618 within the receptacle 616 tapers to a diameter equal to the diameter of the distal end of the motor drive shaft 184. Thus, when the distal end of the motor drive shaft 184 is inserted into the receptacle 616, it is guided into an interference fitted with the coil spring 206.

The operation of the clutch assembly 600 is identical to that of the clutch assembly 200, with the exception that the coil spring 206 frictionally interacts with the motor drive shaft 184 of the driver member 604, rather than the boss 212 of the driven member 202.

Figure 9:
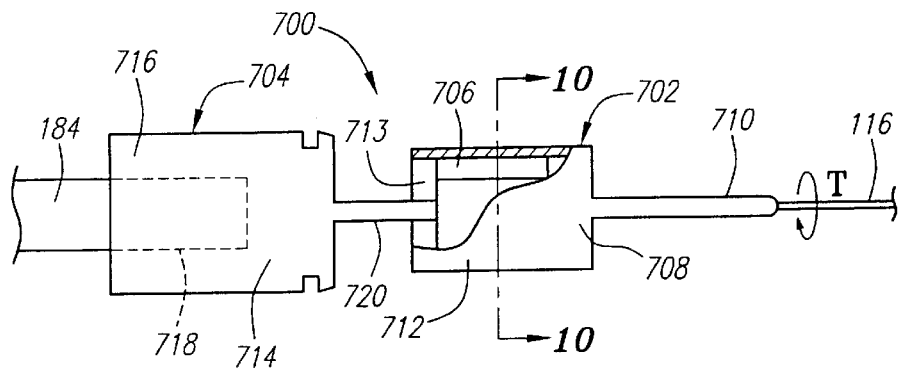
FIG. 9 is a partially cut-away side view of a sixth preferred embodiment of an automatic clutch assembly employed in the imaging system of FIG. 1.
Figure 10:
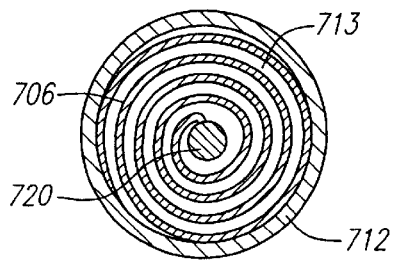
FIG. 10 is a cross-sectional view taken along the line 10—10 of FIG. 9.

FIGS. 9 and 10 depict another alternative embodiment of an automatic clutch assembly 700, which is constructed in accordance with the present inventions. Like the clutch assembly 200 described above, the clutch assembly 700 allows the drive cable 116 to be alternately operated between the drive mode and the release mode, as dictated by the magnitude of the applied torque T. To this end, the clutch assembly 700 includes a driven member 702 and a driver member 704, which are conditionally affixed to each other. That is, the driven member 702 is rotatably engaged with the driver member 704 before the current magnitude of the applied torque T exceeds the critical magnitude, and is rotatably disengaged from the driver member 704 after the current magnitude of the applied torque T exceeds the critical magnitude. Unlike the clutch assembly 200, however, the clutch assembly 700 utilizes a watch spring 706, rather than the coil spring 206, to effect the frictional clutching action.

Specifically, the driver member 704 comprises a generally cylindrical rigid member 714, which is molded from a suitably rigid material, e.g., plastic. The cylindrical member 714 includes a proximally facing receptacle 716 with a cavity 718 formed therein for receiving the distal end of a rigid motor drive shaft 184 from the MDU 104, when the catheter hub 132 is mated with the MDU hub 186 (shown in FIG. 2). To facilitate proper and firm engagement with the motor drive shaft 184, the receptacle 716 and motor drive shaft 184 are keyed, such that the receptacle 716 rotatably engages the motor drive shaft 184 when inserted into the cavity 718. The cylindrical member 714 further includes a distally facing transitional shaft 720 and the watch spring 706, which is wound around the transitional shaft 720, with one end of the watch spring 706 being suitably bonded to the transitional shaft 720 (best shown in FIG. 10).

The driven member 702 comprises a generally cylindrical rigid member 708, which is composed of a suitable rigid material, e.g., stainless steel. The cylindrical member 708 includes an elongate shaft 710 with a proximally facing receptacle 712 having a cavity 713 formed therein. The receptacle 712 and the shaft 710 can be molded as an integral unit, or can alternatively be affixed to each other using suitable means, e.g., welding.

The watch spring 706 provides the means for effecting the aforementioned clutching action. Specifically, the watch spring 706 is interference fitted within the cavity 713, such that a frictionally engaging relationship is formed between the watch spring 706 and the receptacle 712. In this regard, the normal outer diameter (the outer diameter in the absence of an external force) of the watch spring 706 is greater than the inner diameter of the cavity 713. Preferably, the cavity 713 is polished to a substantially uniform diameter to provide a substantially uniform contact between the watch spring 706 and the receptacle 712. The watch spring 706 is preferably wound in a direction, such that it tends to "wind" in the presence of the applied torque T. That is, the interference fit between the watch spring 706 and the receptacle 712 decreases as the applied torque T increases. In the illustrated embodiment, the watch spring 706 is wound in the counterclockwise direction from the inside.

The operation of the clutch assembly 700 is similar to that of the clutch assembly 200 described with respect to FIG. 5. Specifically, as long as the critical magnitude is not exceeded, the current magnitude of the applied torque T does not overcome the frictional force generated by the interference fit between the watch spring 706 and the receptacle 712 (in spite of the reduced interference fit due to the "winding" of the watch spring 706 in the presence of the applied torque T). Thus, the driven member 702 remains rotatably engaged with the driver member 704. As a result, the drive cable 116 is rotatably coupled to, and integrally rotates with, the motor drive shaft 184. That is, the drive cable 116 is operated in the drive mode.

Once the critical magnitude is exceeded, the current magnitude of the applied torque T overcomes the frictional force generated by the interference fit between the watch spring 706 and the receptacle 712 (facilitated by the decrease in the interference fit due to the "winding" of the watch spring 706 in the presence of the applied torque T). Thus, the driven member 702 becomes rotatably disengaged with the driver member 704. As a result, the drive cable 116 is rotatably uncoupled from, and does not integrally rotate with, the motor drive shaft 184. That is, the drive cable 116 is operated in the release mode.

Figure 11:
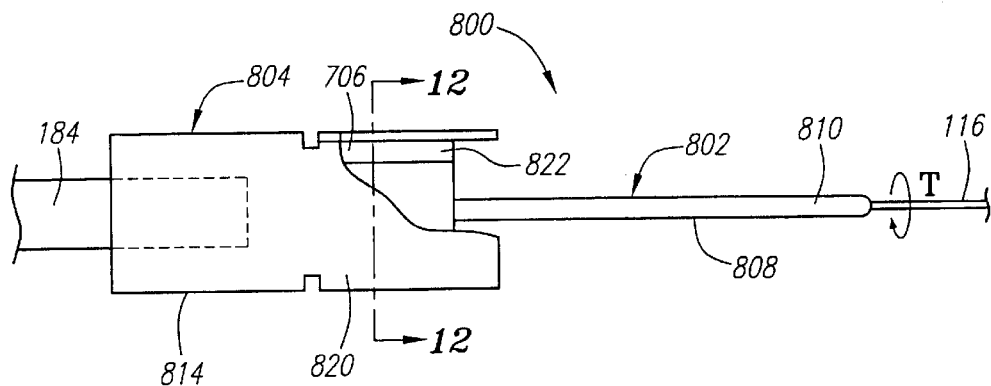
FIG. 11 is a partially cut-away side view of a seventh preferred embodiment of an automatic clutch assembly employed in the imaging system of FIG. 1.
Figure 12:
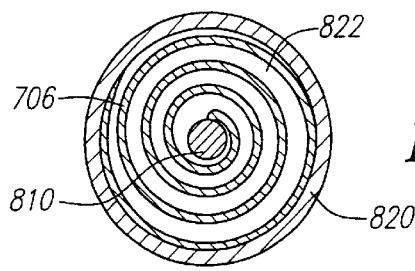
FIG. 12 is a cross-sectional view taken along the line 12—12 of FIG. 11.

FIGS. 11 and 12 depict another alternative embodiment of an automatic clutch assembly 800, which is constructed in accordance with the present inventions. Like the clutch assembly 700 described above, the clutch assembly 800 includes a driven member 802 and a driver member 804 that are conditionally affixed to each other, wherein the clutching function of the clutch assembly 800 is frictionally actuated by the watch spring 706. The clutch assembly 800 differs from the clutch assembly 700, however, in that the driven member 802, rather than the driver member 804, includes the watch spring 706.

Specifically, the driven member 802 includes a generally cylindrical rigid member 808, which is constructed similarly to the above-described cylindrical member 708 (see FIG. 9), with the exception that the cylindrical member 808 does not include a receptacle 712. Thus, the cylindrical member 808 is formed solely by an elongate shaft 810. The driven member 802 further includes the watch spring 706, which is wound around the proximal end of the shaft 810, with one end of the watch spring 706 being suitably bonded to the shaft 810 (best shown in FIG. 12).

The driver member 804 includes a generally cylindrical rigid member 814, which is constructed similarly to the above-described cylindrical member 714 (see FIG. 9), with the exception that the cylindrical member 814 includes a distally facing receptacle 820 having a cavity 822 formed therein, rather than the transitional shaft 720. The watch spring 706 is interference fitted within the cavity 822 in the same manner as that described above with respect to the watch spring 706 and the cavity 714 of the receptacle 712 (see FIG. 9). Again, the watch spring 706 is preferably wound in a direction, such that it tends to "wind" in the presence of the applied torque T. In the illustrated embodiment, the watch spring 706 is wound in the clockwise direction from the inside.

The operation of the clutch assembly 800 is identical to that of the clutch assembly 700, with the exception that the watch spring 706 friction ally interact s with the receptacle 820 of the driver member 804, rather than the receptacle 712 of the driven member 702.

Figure 13:
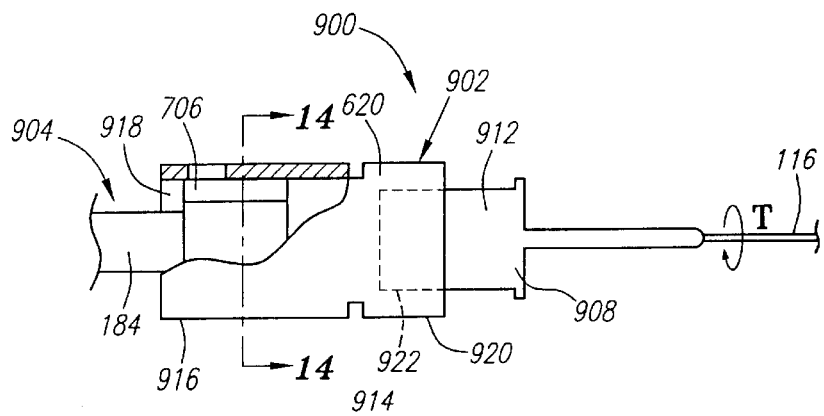
FIG. 13 is a partially cut-away side view of an eighth preferred embodiment of an automatic clutch assembly employed in the imaging system of FIG. 1.
Figure 14:
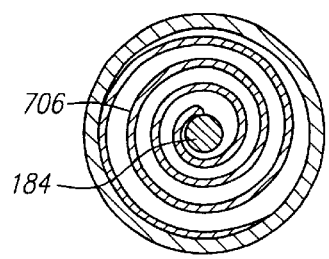
FIG. 14 is a cross-sectional view taken along the line 14—14 of FIG. 13.

FIGS. 13 and 14 depict another alternative embodiment of an automatic clutch assembly 900, which is constructed in accordance with the present invention. Like the clutch assembly 700 described above, the clutch assembly 900 includes a driven member 902 and a driver member 904 that are conditionally affixed to each other. The clutch assembly 900 differs from the clutch assembly 200, however, in that the driver member 904 resides in the MDU 104, rather than in the catheter hub 132 (shown in FIG. 1).

Specifically, the driver member 904 comprises the motor drive shaft 184 itself. The driver member 904 further includes the watch spring 706, which is wound around the distal end of the drive shaft 184, with one end of the watch spring 706 being suitably bonded to the motor drive shaft 184 (best shown in FIG. 14).

The driven member 902 includes a generally cylindrical rigid member 908, which is constructed similarly to the above-described cylindrical member 708 (see FIG. 9), with the exception that the cylindrical member 908 includes a proximally facing boss 912, rather than the receptacle 712. The driven member 902 further includes a generally cylindrical rigid member 914, which is molded from a suitably rigid material, e.g., plastic. The cylindrical member 914 includes a distally facing receptacle 920 with a cavity 922 formed therein, wherein the boss 912 (shown partially in phantom in FIG. 13) of the cylindrical member 908 is mounted by suitable means, e.g., bonding. Like the above-described cylindrical member 714 (see FIG. 9), the cylindrical member 914 further includes a proximally facing receptacle 916 with a cavity 918 formed therein for receiving the distal end of a rigid motor drive shaft 184 from the MDU 104, when the catheter hub 132 is mated with the MDU hub 186 (shown in FIG. 2).

The watch spring 706 is interference fitted within the cavity 918 in the same manner as that described above with respect to the watch spring 706 and the cavity 713 of the receptacle 712 (see FIG. 9). Again, the watch spring 706 is preferably wound in a direction, such that it tends to "wind" in the presence of the applied torque T. In the illustrated embodiment, the watch spring 706 is wound in the counterclockwise direction from the inside.

The operation of the clutch assembly 900 is identical to that of the clutch assembly 700, with the exception that the watch spring 706 frictionally interacts with the receptacle 916 of the driven member 902, rather than the receptacle 712 of the driven member 702.

Figure 15:
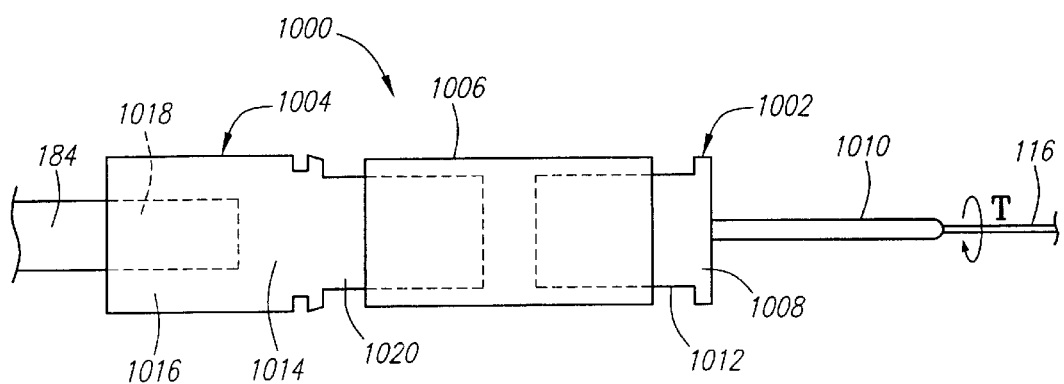
FIG. 15 is a side view of a ninth preferred embodiment of an automatic clutch assembly employed in the imaging system of FIG. 1.

FIG. 15 depicts another alternative embodiment of an automatic clutch assembly 1000, which is constructed in accordance with the present inventions. Like the clutch assemblies 200 and 700 described above, the clutch assembly 1000 allows the drive cable 116 to be alternately operated between the drive mode and the release mode, as dictated by the magnitude of the applied torque T. To this end, the clutch assembly 1000 includes a driven member 1002 and a driver member 1004, which are conditionally affixed to each other. That is, the driven member 1002 is rotatably engaged with the driver member 1004 before the current magnitude of the applied torque T exceeds the critical magnitude, and is rotatably disengaged from the driver member 1004 after the current magnitude of the applied torque T exceeds the critical magnitude. Unlike the clutch assemblies 200 and 700, however, the clutch assembly 1000 utilizes a compliant member 1006, rather than a spring, to effect the frictional clutching action.

Specifically, the driver member 1004 comprises a generally cylindrical rigid member 1014, which is molded from a suitably rigid material, e.g., plastic. The cylindrical member 1014 includes a proximally facing receptacle 1016 with a cavity 1018 formed therein for receiving the distal end of a rigid motor drive shaft 184 from the MDU 104, when the catheter hub 132 is mated with the MDU hub 186 (shown in FIG. 2). To facilitate proper and firm engagement with the motor drive shaft 184, the receptacle 1016 and motor drive shaft 184 are keyed, such that the receptacle 1016 rotatably engages the motor drive shaft 184 when inserted into the cavity 1018. The cylindrical member 1014 further includes a distally facing transitional shaft 1020 and the compliant tube 1006, which is composed of a suitably compliant material, e.g., rubber or silicone. The proximal end of the compliant tube 1006 is disposed over and suitably bonded to the transitional shaft 1020.

The driven member 1002 comprises a generally cylindrical rigid member 1008, which is composed of a suitable rigid material, e.g., stainless steel. The cylindrical member 1008 includes an elongate shaft 1010 with a proximally facing boss 1012. The boss 1012 and the shaft 1010 can be molded as an integral unit, or can alternatively be affixed to each other using suitable means, e.g., welding.

The compliant tube 1016 provides the means for effecting the aforementioned clutching action. Specifically, the distal end of the compliant tube 1006 is interference fitted over the boss 1012, such that a frictionally engaging relationship is formed therebetween. In this regard, the normal outer diameter (the outer diameter in the absence of an external force) of the compliant tube 1006 is less than the outer diameter of the boss 1012. Preferably, the boss 1012 is polished to a substantially uniform diameter to provide a substantially uniform contact between the compliant tube 1006 and the boss 1012. Because the inner diameters of the proximal and distal ends of the compliant tube 1006 are the same, the outer diameter of the boss 1012 is preferably equal to the outer diameter of the transitional shaft 1020.

Although the compliant tube 1006 in the illustrated embodiment is conditionally affixed to the boss 1012, the compliant tube 1006 can alternatively be conditionally affixed to the transitional shaft 1020. That is, the distal end of the compliant tube 1006 can be disposed over and suitably bonded to the boss 1012, and the proximal end of the compliant tube 1006 can be interference fitted over the boss 1012, such that a frictionally engaging relationship is formed therebetween.

The operation of the clutch assembly 1000 is similar to that of the clutch assembly 200 described with respect to FIG. 5. Specifically, as long as the critical magnitude is not exceeded, the current magnitude of the applied torque T does not overcome the frictional force generated by the interference fit between the compliant tube 1006 and the boss 1012 (or the compliant tube 1006 and the transitional shaft 1020 if the compliant tube 1006 is conditionally affixed to the transitional shaft). Thus, the driven member 1002 remains rotatably engaged with the driver member 1004. As a result, the drive cable 116 is rotatably coupled to, and integrally rotates with, the motor drive shaft 184. That is, the drive cable 116 is operated in the drive mode.

Once the critical magnitude is exceeded, the current magnitude of the applied torque T overcomes the frictional force generated by the interference fit between the compliant tube 1006 and the boss 1012 (or the compliant tube 1006 and the transitional shaft 1020 if the compliant tube 1006 is conditionally affixed to the transitional shaft). Thus, the driven member 1002 becomes rotatably disengaged with the driver member 1004. As a result, the drive cable 116 is rotatably uncoupled from, and does not integrally rotate with, the motor drive shaft 184. That is, the drive cable 116 is operated in the release mode.

Figure 16:
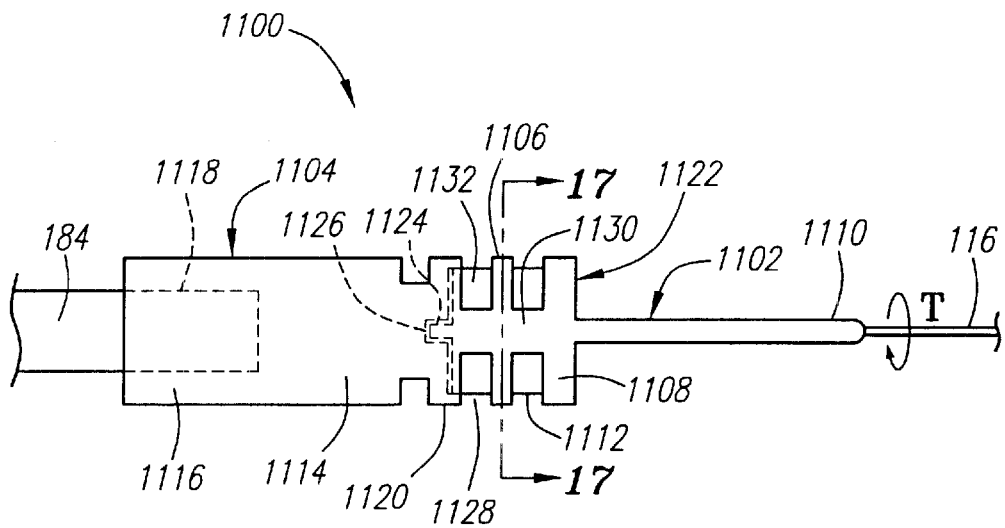
FIG. 16 is a side view of a tenth preferred embodiment of an automatic clutch assembly employed in the imaging system of FIG. 1.
Figure 17:
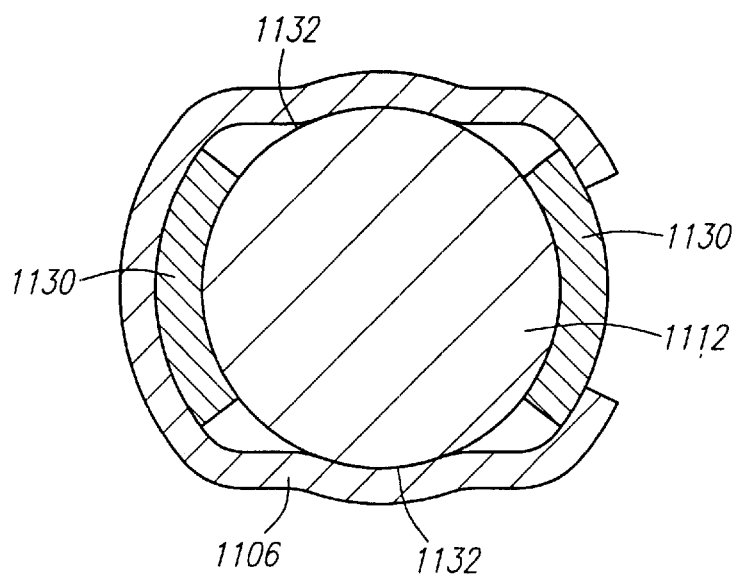
FIG. 17 is a cross-sectional view taken along the line 17—17 of FIG. 16.

FIGS. 16 and 17 depict another alternative embodiment of an automatic clutch assembly 1100, which is constructed in accordance with the present inventions. Like the clutch assemblies 200, 700, and 1000 described above, the clutch assembly 1100 allows the drive cable 116 to be alternately operated between the drive mode and the release mode, as dictated by the magnitude of the applied torque T. To this end, the clutch assembly 1100 includes a driven member 1102 and a driver member 1104, which are conditionally affixed to each other. That is, the driven member 1102 is rotatably engaged with the driver member 1104 before the current magnitude of the applied torque T exceeds the critical magnitude, and is rotatably disengaged from the driver member 1104 after the current magnitude of the applied torque T exceeds the critical magnitude. Unlike the clutch assemblies 200, 700, and 1000, however, the clutch assembly 1100 utilizes rigid bodies to effect the frictional clutching action.

Specifically, the driver member 1104 comprises a generally cylindrical rigid member 1114, which is molded from a suitably rigid material, e.g., plastic. The cylindrical member 1114 includes a proximally facing receptacle 1116 with a cavity 1118 formed therein for receiving the distal end of a rigid motor drive shaft 184 from the MDU 104, when the catheter hub 132 is mated with the MDU hub 186 (shown in FIG. 2). To facilitate proper and firm engagement with the motor drive shaft 184, the receptacle 1116 and motor drive shaft 184 are keyed, such that the receptacle 1116 rotatably engages the motor drive shaft 184 when inserted into the cavity 1118. The cylindrical member 1114 further includes a distally facing receptacle 1120 with a cavity 1122 formed therein.

The driven member 1102 comprises a generally cylindrical rigid member 1108, which is composed of a suitable rigid material, e.g., stainless steel. The cylindrical member 1108 includes an elongate shaft 1110 with a proximally facing boss 1112. The boss 1112 and the shaft 1110 can be molded as an integral unit, or can alternatively be affixed to each other using suitable means, e.g., welding The boss 1112 is disposed within the cavity 1122 of the receptacle 1120, with the outer diameter of the boss 1112 being slightly less than the diameter of the cavity 1122, such that, absent any external binding force, the boss 1112 can rotate freely within the cavity 1122. To facilitate axial alignment between the driven member 1102 and driver member 1104, the proximal face of the boss 1112 includes a centered pin 1124 (shown in phantom in FIG. 16), and the receptacle 1120 includes a centered pin hole 1126 (also shown in phantom) proximally adjacent the cavity 1122, wherein the pin 1124 and pin hole 1126 engage each other to center the boss 1112 within the cavity 1122 of the receptacle 1120.

The spring clamp 1106 is interference fit about the receptacle 1120 and boss 1112 to provide a binding force between the receptacle 1120 and boss 1112. Specifically, the longitudinal center of the receptacle 1120 includes a pair of opposing circumferential cutouts 1128 and a pair of adjacent bridge sections 1130. Thus, the boss 1112 includes a pair of opposing arcuate surfaces 1132 that is exposed through the respective cutouts 1128. The spring clamp 1106 is interference fit around the pair of bridge sections 1130 and the pair of exposed arcuate surfaces 1132, such that a frictionally engaging relationship is formed among the spring clamp 1106, receptacle 1120, and boss 1112.

Once the critical magnitude is exceeded, the current magnitude of the applied torque T overcomes the frictional force generated by the interference fit among the spring clamp 1106, receptacle 1120, and boss 1112. Thus, the driven member 1102 becomes rotatably disengaged with the driver member 1104. As a result, the drive cable 116 is rotatably uncoupled from, and does not integrally rotate with, the motor drive shaft 184. That is, the drive cable 116 is operated in the release mode.

Figure 18:
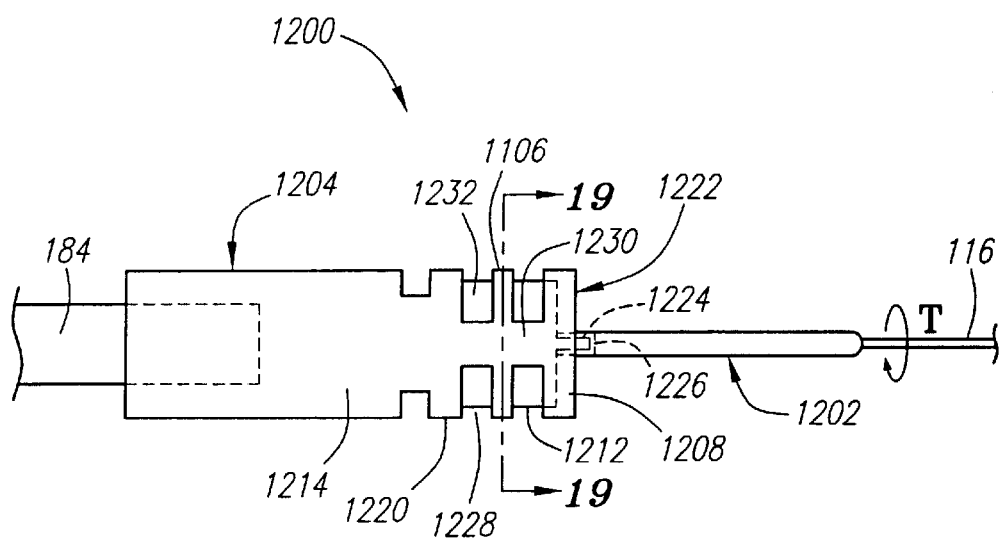
FIG. 18 is a side view of an eleventh preferred embodiment of an automatic clutch assembly employed in the imaging system of FIG. 1.
Figure 19:
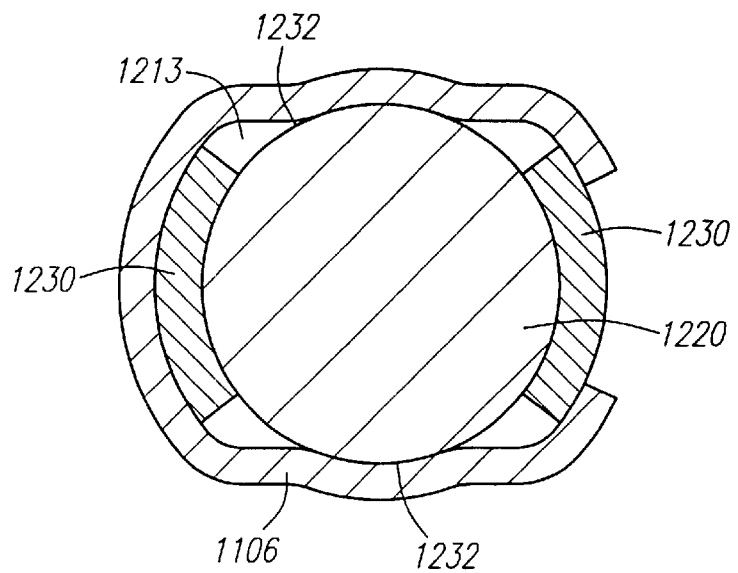
FIG. 19 is a cross-sectional view taken along the line 19—19 of FIG. 18.

FIGS. 18 and 19 depict another alternative embodiment of an automatic clutch assembly 1200, which is constructed in accordance with the present inventions. Like the clutch assembly 1100 described above, the clutch assembly 1200 includes a driven member 1202 and a driver member 1204 that are conditionally affixed to each other, wherein the clutching function of the clutch assembly 1200 is frictionally actuated by the spring clamp 1106. The clutch assembly 1200 differs from the clutch assembly 1100, however, in that the driven member 1202 houses the driver member 1204, rather than vice versa.

Specifically, the driven member 1202 includes a generally cylindrical rigid member 1208, which is constructed similarly to the above-described cylindrical member 1108 (see FIG. 16), with the exception that the cylindrical member 1208 includes a proximally facing receptacle 1212 having a cavity 1213 formed therein, rather than the boss 1112. The driver member 1204 includes a generally cylindrical rigid member 1214, which is constructed similarly to the above-described cylindrical member 1114 (see FIG. 16), with the exception that the cylindrical member 1214 includes a distally facing transitional shaft 1220, rather than the transitional shaft 1120.

The transitional shaft 1220 is disposed within the cavity 1213 of the receptacle 1212, with the outer diameter of the transitional shaft 1220 being slightly less than the diameter of the cavity 1213, such that, absent any external binding force, the transitional shaft 1220 can rotate freely within the cavity 1213. To facilitate axial alignment between the driven member 1202 and driver member 1204, the distal face of the transitional shaft 1220 includes a centered pin 1224 (shown in phantom in FIG. 18), and the receptacle 1212 includes a centered pin hole 1226 (also shown in phantom in FIG. 18) distally adjacent the cavity 1213, wherein the pin 1224 and pin hole 1226 engage each other to center the transitional shaft 1220 within the cavity 1213 of the receptacle 1212.

The spring clamp 1106 is interference fit about the receptacle 1212 and transitional shaft 1220 to provide a binding force between the receptacle 1212 and transitional shaft 1220. Specifically, the longitudinal center of the receptacle 1212 includes a pair of opposing circumferential cutouts 1228 and a pair of adjacent bridge sections 1230. Thus, the transitional shaft 1220 includes a pair of opposing arcuate surfaces 1232 that is exposed through the respective cutouts 1228. The spring clamp 1106 is interference fit around the pair of bridge sections 1230 and the pair of exposed arcuate surfaces 1232, such that a frictionally engaging relationship is formed among the spring clamp 1106, receptacle 1212, and transitional shaft 1220.

The operation of the clutch assembly 1200 is identical to that of the clutch assembly 1100, with the exception that the spring clamp 1106, the receptacle 1212 of the driven member 1202, and transitional shaft 1220 of the driver member 1204 frictionally interact with each other, rather than the spring clamp 1106, receptacle 1120 of the driver member 1104, and boss 1112 of the driven member 1102.

Figure 20:
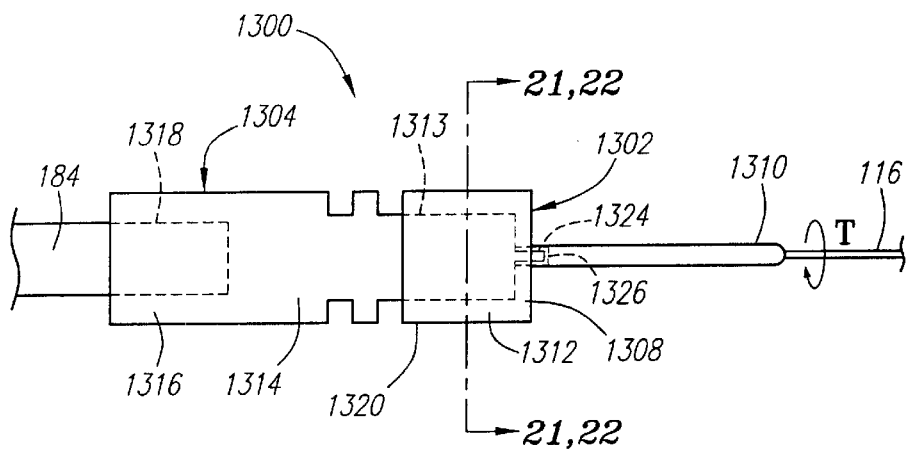
FIG. 20 is a side view of a twelfth preferred embodiment of an automatic clutch assembly employed in the imaging system of FIG. 1.
Figure 21:
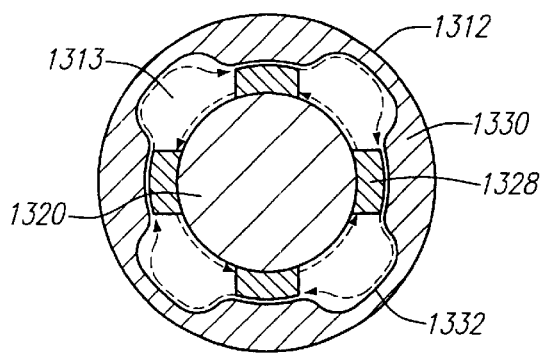
FIG. 21 is a cross-sectional view taken along the line 21—21 of FIG. 20.
Figure 22:
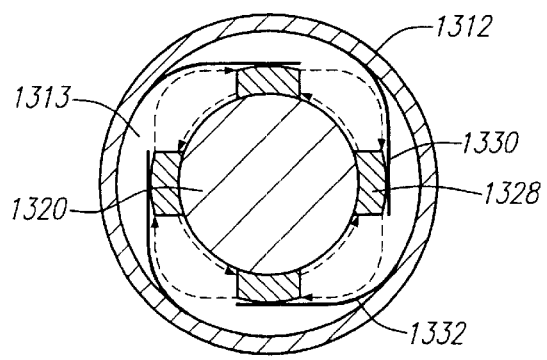
FIG. 22 is a cross-sectional view taken along the line 22—22 of FIG. 20.

FIGS. 20–22 depict another alternative embodiment of an automatic clutch assembly 1300, which is constructed in accordance with the present inventions. Like the clutch assemblies 200, 700, 1000, and 1100 described above, the clutch assembly 1300 allows the drive cable 116 to be alternately operated between the drive mode and the release mode, as dictated by the magnitude of the applied torque T. To this end, the clutch assembly 1300 includes a driven member 1302 and a driver member 1304, which are conditionally affixed to each other. That is, the driven member 1302 is rotatably engaged with the driver member 1304 before the current magnitude of the applied torque T exceeds the critical magnitude, and is rotatably disengaged from the driver member 1304 after the current magnitude of the applied torque T exceeds the critical magnitude. Unlike the clutch assemblies 200, 700, 1000, and 1100, however, the clutch assembly 1300 utilizes magnetic forces, rather than frictional forces, to effect the clutching action.

Specifically, the driver member 1304 comprises a generally cylindrical rigid member 1314, which is molded from a ferrous material. The cylindrical member 1314 includes a proximally facing receptacle 1316 with a cavity 1318 formed therein for receiving the distal end of a rigid motor drive shaft 184 from the MDU 104, when the catheter hub 132 is mated with the MDU hub 186 (shown in FIG. 2). To facilitate proper and firm engagement with the motor drive shaft 184, the receptacle 1316 and motor drive shaft 184 are keyed, such that the receptacle 1316 rotatably engages the motor drive shaft 184 when inserted into the cavity 1318. The cylindrical member 1314 further includes a distally facing transitional shaft 1320.

The driven member 1302 comprises a generally cylindrical rigid member 1308, which is composed of a suitable rigid material, e.g., stainless steel. The cylindrical member 1308 includes an elongate shaft 1310 with a proximally facing receptacle 1312. having a cavity 1313 formed therein. The receptacle 1312 and the shaft 1310 can be molded as an integral unit, or can alternatively be affixed to each other using suitable means, e.g., welding.

The transitional shaft 1320 is disposed within the cavity 1313 of the receptacle 1312. To facilitate axial alignment between the driven member 1302 and driver member 1304, the distal face of the transitional shaft 1320 includes a centered pin 1324 (shown in phantom in FIG. 20), and the receptacle 1312 includes a centered pin hole 1326 (also shown in phantom) distally adjacent the cavity 1313, wherein the pin 1324 and pin hole 1326 engage each other to center the transitional shaft 1320 within the cavity 1313 of the receptacle 1312.

A magnetic system provides the means for effecting the aforementioned clutching action. Specifically, the transitional shaft 1320 of the cylindrical member 1314 is composed of a ferrous material, and includes four outwardly extending permanent magnets 1328, which are circumferentially affixed about the transitional shaft 1320 by suitable means, e.g., bonding. In the illustrated embodiment, adjacent magnets 1328 are separated by 90° and substantially extend the length of the transitional shaft 1320. As can be seen, each magnet 1328 includes a north pole N and a south pole S, with the polarities of each magnet 1328 being opposite with respect to the two adjacent magnets 1328.

The receptacle 1312 of the cylindrical member 1308 is composed of a ferrous material, and includes four inwardly extending ferrous elements 1330 and four outwardly extending ferrous arcs 1332, which are circumferentially disposed about the cavity 1313. In the illustrated embodiment, adjacent ferrous elements 1330 are separated by 90° and substantially extend the length of the receptacle 1312. The ferrous arcs 1332 are interlaced between the ferrous elements 1330, and likewise, are separated by 90° and substantially extend the length of the receptacle 1312. In the embodiment illustrated in FIG. 21, the ferrous elements 1330 and arcs 1332 are formed from the deformed inner surface of the receptacle 1312. In an alternative embodiment illustrated in FIG. 22, the ferrous elements 1330 and arcs 1332 are formed from four curvilinear flanges.

The four ferrous elements 1330 are located outwardly adjacent the four magnets 1328, respectively, such that a magnetically engaging relationship is formed between the magnets 1328 and ferrous elements 1330. As can be seen, the transitional shaft 1320, by virtue of its ferrous composition, advantageously provides a magnetic return (indicated by arrows) between the inward poles of adjacent magnets 1328, and the receptacle 1312, by virtue of its ferrous composition, provides a magnetic return (indicated by arrows) between the outward poles of adjacent magnets 1328. The outwardly extending arcs 1332 facilitate the magnetically engaging relationship between the magnets 1328 and ferrous elements 1330, by concentrating the magnetic force at the ferrous elements 1330.

The operation of the clutch assembly 1300 is similar to that of the clutch assembly 200 described with respect to FIG. 5. Specifically, as long as the critical magnitude is not exceeded, the current magnitude of the applied torque T does not overcome the attractive magnetic force generated between the magnets 1328 and ferrous elements 1330. Thus, the driven member 1302 remains rotatably engaged with the driver member 1304. As a result, the drive cable 116 is rotatably coupled to, and integrally rotates with, the motor drive shaft 184. That is, the drive cable 116 is operated in the drive mode.

Once the critical magnitude is exceeded, the current magnitude of the applied torque T overcomes the attractive magnetic force generated between the magnets 1328 and ferrous elements 1330. Thus, the driven member 1302 becomes rotatably disengaged with the driver member 1304. As a result, the drive cable 116 is rotatably uncoupled from, and does not integrally rotate with, the motor drive shaft 184. That is, the drive cable 116 is operated in the release mode.

Figure 23:
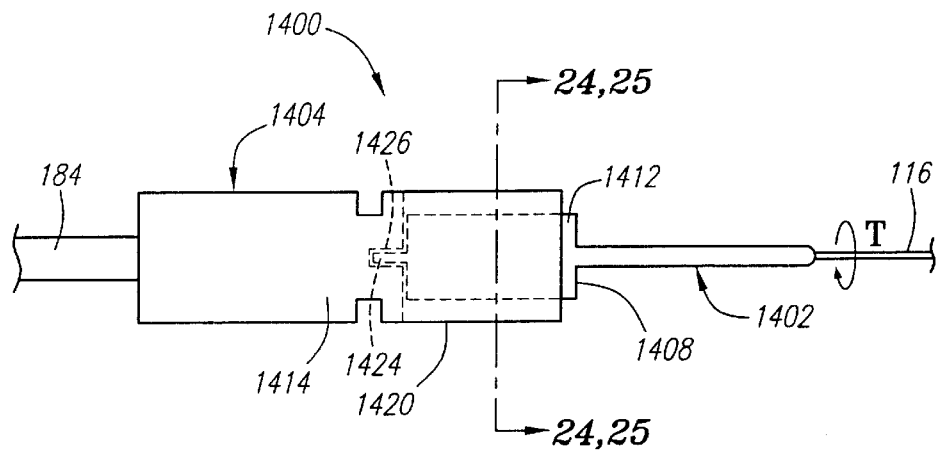
FIG. 23 is a side view of a thirteenth preferred embodiment of an automatic clutch assembly employed in the imaging system of FIG. 1.
Figure 24:
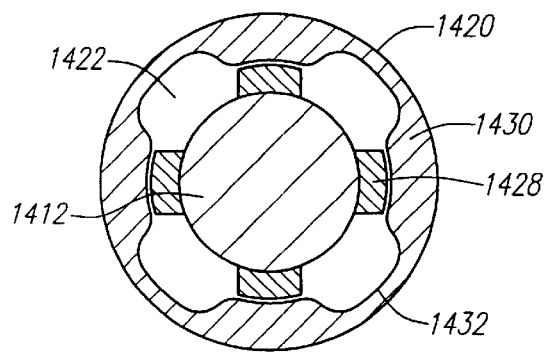
FIG. 24 is a cross-sectional view taken along the line 24—24 of FIG. 23.
Figure 25:
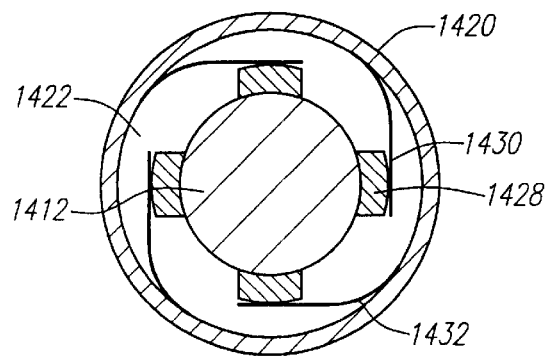
FIG. 25 is a cross-sectional view taken along the line 25—25 of FIG. 23.

FIGS. 23–25 depict another alternative embodiment of an automatic clutch assembly 1400, which is constructed in accordance with the present inventions. Like the clutch assembly 1300 described above, the clutch assembly 1400 includes a driven member 1402 and a driver member 1404 that are conditionally affixed to each other, wherein the clutching function of the clutch assembly 1400 is magnetically actuated. The clutch assembly 1400 differs from the clutch assembly 1300, however, in that the driver member 1404 houses the driven member 1402, rather than vice versa. Also, the driven member 1402 is magnetic and the driver member 1404 is ferrous, rather than vice versa.

Specifically, the driven member 1402 includes a generally cylindrical rigid member 1408, which is constructed similarly to the above-described cylindrical member 1308 (see FIG. 20), with the exception that the cylindrical member 1408 includes a proximally facing boss 1412, rather than the receptacle 1312. The driver member 1404 includes a generally cylindrical rigid member 1414, which is constructed similarly to the above-described cylindrical member 1314 (see FIG. 20), with the exception that the cylindrical member 1414 includes a distally facing receptacle 1420 with a cavity 1422 formed therein, rather than the transitional shaft 1320.

The boss 1412 is disposed within the cavity 1422 of the receptacle 1420. To facilitate axial alignment between the driven member 1402 and driver member 1404, the distal face of the boss 1412 includes a centered pin 1424 (shown in phantom in FIG. 23), and the receptacle 1420 includes a centered pin hole 1426 (also shown in phantom in FIG. 23) proximally adjacent the cavity 1422, wherein the pin 1424 and pin hole 1426 engage each other to center the boss 1412 within the cavity 1422 of the receptacle 1420. The boss 1412 is composed of a ferrous material, and includes four outwardly extending permanent magnets 1428, which are circumferentially affixed about the boss 1412 by suitable means, e.g., bonding.

The receptacle 1420 is composed of a ferrous material, and includes four inwardly extending ferrous elements 1430 and four outwardly extending ferrous arcs 1432, which are circumferentially disposed about the cavity 1422. In the embodiment illustrated in FIG. 24, the ferrous elements 1430 and arcs 1432 are formed from the deformed inner surface of the receptacle 1420. In an alternative embodiment illustrated in FIG. 25, the ferrous elements 1430 and arcs 1432 are formed from four curvilinear flanges.

The four ferrous elements 1430 are located outwardly adjacent the four magnets 1428, respectively, such that a magnetically engaging relationship is formed between the magnets 1428 and ferrous elements 1430. As can be seen, the boss 1412, by virtue of its ferrous composition, advantageously provides a magnetic return (indicated by arrows) between the inward poles of adjacent magnets 1428, and the receptacle 1420, by virtue of its ferrous composition, provides a magnetic return (indicated by arrows) between the outward poles of adjacent magnets 1428. The outwardly extending arcs 1432 facilitate the magnetically engaging relationship between the magnets 1428 and ferrous elements 1430, by concentrating the magnetic force at the ferrous elements 1430.

The operation of the clutch assembly 1400 is identical to that of the clutch assembly 1300, with the exception that the magnets 1428 of the driven member 1402 and the ferrous elements 1430 of the driver member 1404 magnetically interact with each other, rather than the magnets 1328 of the driver member 1304 and the ferrous elements 1330 of the driven member 1302.

Figure 26:
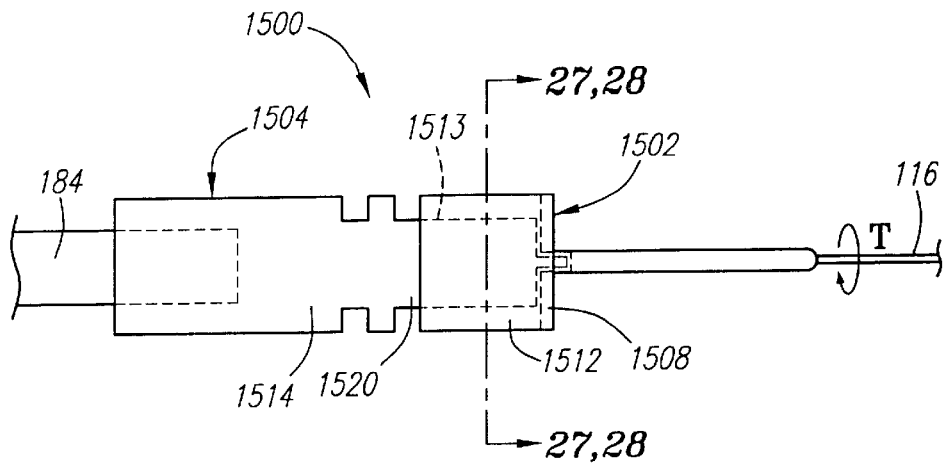
FIG. 26 is a side view of a fourteenth preferred embodiment of an automatic clutch assembly employed in the imaging system of FIG. 1.
Figure 27:
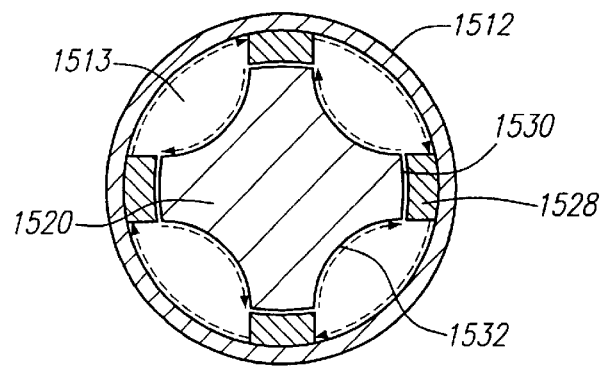
FIG. 27 is a cross-sectional view taken along the line 27—27 of FIG. 26.
Figure 28:
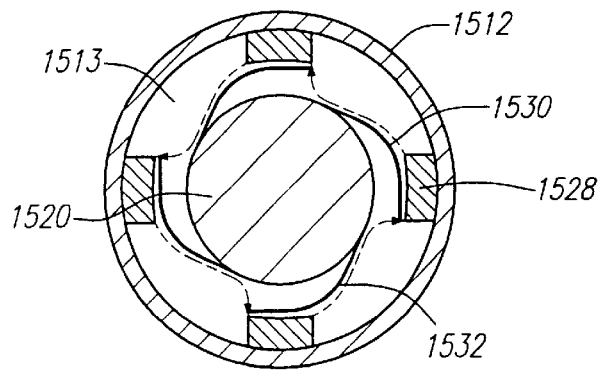
FIG. 28 is a cross-sectional view taken along the line 28—28 of FIG. 26.

FIGS. 26–28 depict another alternative embodiment of an automatic clutch assembly 1500, which is constructed in accordance with the present inventions. Like the clutch assembly 1300 described above, the clutch assembly 1500 includes a driven member 1502 and a driver member 1504 that are conditionally affixed to each other, wherein the clutching function of the clutch assembly 1500 is magnetically actuated. The clutch assembly 1500 differs from the clutch assembly 1300, however, in that the driven member 1502 is magnetic and the driver member 1504 is ferrous, rather than vice versa.

Specifically, the driven member 1502 includes a generally cylindrical rigid member 1508, which is constructed similarly to the above-described cylindrical member 1308 (see FIG. 20), and includes a proximally facing receptacle 1512 having a cavity 1513 formed therein. The driver member 1504 includes a generally cylindrical rigid member 1514, which is constructed similarly to the above-described cylindrical member 1314 (see FIG. 20), and includes a transitional shaft 1520.

The transitional shaft 1520 is disposed within the cavity 1513 of the receptacle 1512. The receptacle 1512 is composed of a ferrous material, and includes four inwardly extending permanent magnets 1528, which are circumferentially disposed around the cavity 1513, and are affixed to the receptacle 1512 by suitable means, e.g., bonding. The transitional shaft 1520 is composed of a ferrous material, and includes four outwardly extending ferrous elements 1530 and four inwardly extending ferrous arcs 1532, which are circumferentially disposed around the transitional shaft 1520. In the embodiment illustrated in FIG. 27, the ferrous elements 1530 and arcs 1532 are formed from the deformed outer surface of the transitional shaft 1520. In an alternative embodiment illustrated in FIG. 28, the ferrous elements 1530 and arcs 1532 are formed from four curvilinear flanges.

The four ferrous elements 1530 are located inwardly adjacent the four magnets 1528, respectively, such that a magnetically engaging relationship is formed between the magnets 1528 and ferrous elements 1530. As can be seen, the receptacle 1512, by virtue of its ferrous composition, advantageously provides a magnetic return (indicated by arrows) between the outward poles of adjacent magnets 1528, and the-transitional shaft 1520, by virtue of its ferrous composition, provides a magnetic return (indicated by arrows) between the inward poles of adjacent magnets 1528. The inwardly extending arcs 1532 facilitate the magnetically engaging relationship between the magnets 1528 and ferrous elements 1530, by concentrating the magnetic force at the ferrous elements 1530.

The operation of the clutch assembly 1500 is identical to that of the clutch assembly 1300, with the exception that the magnets 1528 of the driven member 1502 and the ferrous elements 1530 of the driver member 1504 magnetically interact with each other, rather than the magnets 1328 of the driver member 1304 and the ferrous elements 1330 of the driven member 1302.

Figure 29:
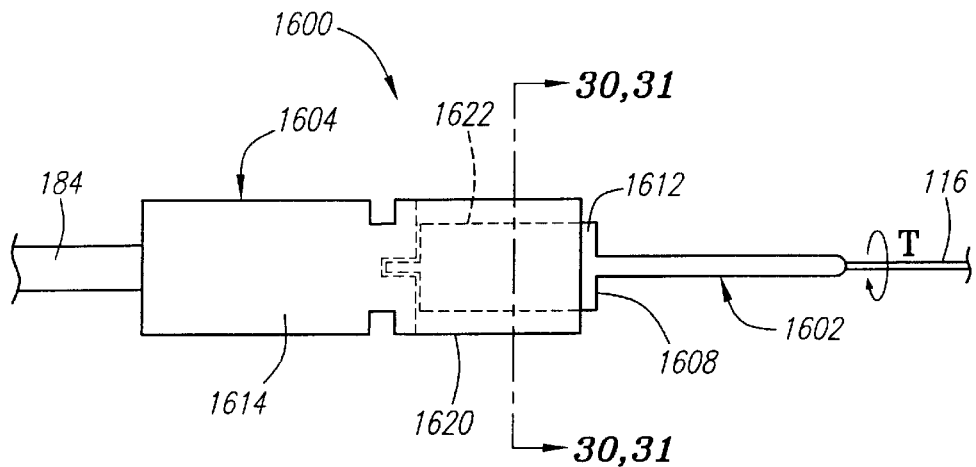
FIG. 29 is a side view of a fifteenth preferred embodiment of an automatic clutch assembly employed in the imaging system of FIG. 1.
Figure 30:
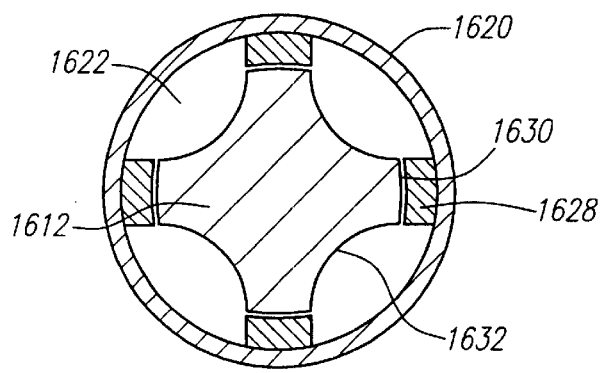
FIG. 30 is a cross-sectional view taken along the line 30—30 of FIG. 29.
Figure 31:
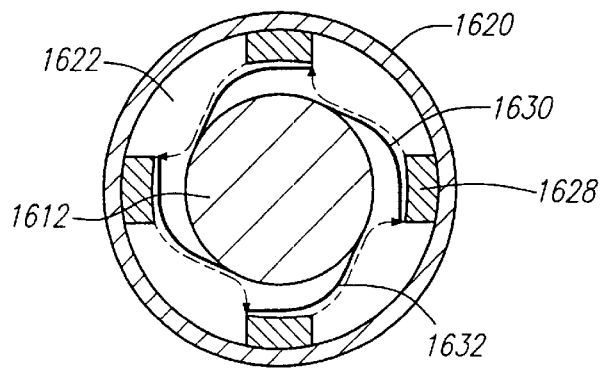
FIG. 31 is a cross-sectional view taken along the line 31—31 of FIG. 29.

FIGS. 29–31 depict another alternative embodiment of an automatic clutch assembly 1600, which is constructed in accordance with the present inventions. Like the clutch assembly 1300 described above, the clutch assembly 1600 includes a driven member 1602 and a driver member 1604 that are conditionally affixed to each other, wherein the clutching function of the clutch assembly 1600 is magnetically actuated. The clutch assembly 1600 differs from the clutch assembly 1300, however, in that the driver member 1604 houses the driven member 1602, rather than vice versa.

Specifically, the driven member 1602 includes a generally cylindrical rigid member 1608, which is constructed similarly to the above-described cylindrical member 1308 (see FIG. 20), with the exception that the cylindrical member 1608 includes a proximally facing boss 1612, rather than a receptacle 1312. The driver member 1604 includes a generally cylindrical rigid member 1614, which is constructed similarly to the above-described cylindrical member 1314 (see FIG. 20), with the exception that the cylindrical member 1614 includes a distally facing receptacle 1620 having a cavity 1622 formed therein, rather than a transitional shaft 1320.

The boss 1612 is disposed within the cavity 1622 of the receptacle 1620. The receptacle 1620 is composed of a ferrous material, and includes four inwardly extending permanent magnets 1628, which are circumferentially disposed around the cavity 1622, and are affixed to the receptacle 1620 by suitable means, e.g., bonding. The boss 1612 is composed of a ferrous material, and includes four outwardly extending ferrous elements 1630 and four inwardly extending ferrous arcs 1632, which are circumferentially disposed around the boss 1612. In the embodiment illustrated in FIG. 30, the ferrous elements 1630 and arcs 1632 are formed from the deformed outer surface of the boss 1612. In an alternative embodiment illustrated in FIG. 31, the ferrous elements 1630 and arcs 1632 are formed from four curvilinear flanges.

The four ferrous elements 1630 are located inwardly adjacent the four magnets 1628, respectively, such that a magnetically engaging relationship is formed between the magnets 1628 and ferrous elements 1630. As can be seen, the receptacle 1620, by virtue of its ferrous composition, advantageously provides a magnetic return (indicated by arrows) between the outward poles of adjacent magnets 1628, and the boss 1612, by virtue of its ferrous composition, provides a magnetic return (indicated by arrows) between the inward poles of adjacent magnets 1628. The inwardly extending arcs 1632 facilitate the magnetically engaging relationship between the magnets 1628 and ferrous elements 1630, by concentrating the magnetic force at the ferrous elements 1630.

The operation of the clutch assembly 1600 is identical to that of the clutch assembly 1300, with the exception that the magnets 1628 of the driven member 1602 and the ferrous elements 1630 of the driver member 1604 magnetically interact with each other, rather than the magnets 1328 of the driver member 1304 and the ferrous elements 1330 of the driven member 1302.

With regard to any of the above-described clutch assemblies, the critical magnitude of the applied torque T, i.e., the point at which the driven member and driver member are rotatably uncoupled from each other, can be selected by "tuning" these clutch assemblies, i.e., altering the materials from which the elements are composed, altering the size of or spatial relationship between the elements, etc. To ensure proper clutching action, a simple fixture with a built-in torque watch can be used to apply a measured torque to these clutch assemblies, whereby the critical magnitude of the applied torque can be determined and compared against an optimum critical magnitude.

While preferred embodiments have been shown and described, it will be apparent to one of ordinary skill in the art that numerous alterations may be made without departing from the spirit or scope of the invention. Therefore, the invention is not to be limited except in accordance with the following claims.

What is claimed:

1. A catheter, comprising:

an elongate member;

a catheter drive shaft to which torque can be applied, the catheter drive shaft being rotatably disposed within the elongate member;

a driven member rotatably coupled to the catheter drive shaft, the driven member comprising a first cylindrical body; and a driver member comprising a second cylindrical body in a concentric relationship with the first cylindrical body, wherein the first and second cylindrical bodies are rotatably engaged with each other before the applied torque exceeds a critical magnitude, and rotatably disengaged with each other after the applied torque exceeds the critical magnitude, the driven and driver members adapted to automatically re-engage each other after the applied torque falls below the critical magnitude.

2. The catheter of claim 1, wherein the first cylindrical body comprises a receptacle having a cylindrical cavity formed therein, and the second cylindrical body is disposed within the cavity.

3. The catheter of claim 1, wherein the second cylindrical body comprises a receptacle having a cylindrical cavity formed therein, and the first cylindrical body is disposed within the cavity.

4. The catheter of claim 1, wherein one of the first and second cylindrical bodies is a compliant tube, and the other of the first and second cylindrical bodies is a rigid cylindrical member over which the compliant tube is interference fit.

5. The catheter of claim 1, further comprising a spring clamp, wherein one of the first and second cylindrical bodies is a cylindrical receptacle including a cavity formed therein, the other of the first and second cylindrical bodies is disposed within the cavity, the cylindrical receptacle having one or more cutouts to expose one or more arcuate surfaces of the other of the first and second cylindrical bodies, and the spring clamp is interference fit around the cylindrical receptacle and the one or more exposed arcuate surfaces.

6. A catheter, comprising:

an elongate member;

a catheter drive shaft rotatably disposed within the elongate member;

a compliant tube;

a rigid cylindrical member on which the compliant tube is interference fit;

a driven member comprising one of the compliant tube and rigid cylindrical member; and a driver member comprising the other of the compliant tube and rigid cylindrical member, the driven and driver members adapted to automatically rotatably disengage each other after an applied torque to the catheter drive shaft exceeds a critical magnitude and re-engage each other after the applied torque falls below the critical magnitude.

7. The catheter of claim 6, wherein the driven member comprises the compliant tube, and the driver member comprises the rigid cylindrical member.

8. The catheter of claim 7, wherein the driven member comprises another rigid cylindrical member, and the compliant tube is affixed over the other rigid cylindrical member.

9. The catheter of claim 6, wherein the driven member comprises the rigid cylindrical member, and the driver member comprises the compliant tube.

10. The catheter of claim 9, wherein the driver member comprises another rigid cylindrical member, and the compliant tube is affixed over the other rigid cylindrical member.

11. The catheter of claim 6, wherein the compliant tube is composed of rubber.

12. The catheter of claim 6, wherein the driven member is affixed directly to the catheter drive shaft.

13. The catheter of claim 6, further comprising a proximal catheter hub permanently mounted to the elongate member, wherein the compliant and rigid cylindrical bodies are housed within the proximal catheter hub.

14. The catheter of claim 6, further comprising a distal ultrasonic transducer mounted to the catheter drive shaft.

15. A catheter, comprising:

an elongate member;

a catheter drive shaft rotatably disposed within the elongate member;

a receptacle having a cylindrical cavity formed therein;

a cylindrical body disposed within the cavity, wherein the receptacle has one or more cutouts to expose one or more arcuate surfaces of the cylindrical body;

a spring clamp interference fit around the receptacle and the one or more exposed arcuate surfaces;

a driven member comprising one of the receptacle and cylindrical body;

and a driver member comprising the other of the receptacle and cylindrical body, the driven and driver members adapted to disengage each other after an applied torque to the catheter drive shaft exceeds a critical magnitude and re-engage each other after the applied torque falls below the critical magnitude.

16. The catheter of claim 15, wherein the driven member comprises the receptacle, and the driver member comprises the cylindrical body.

17. The catheter of claim 15, wherein the driven member comprises the cylindrical body, and the driver member comprises the receptacle.

18. The catheter of claim 15, wherein the driven member is affixed directly to the catheter drive shaft.

19. The catheter of claim 15, further comprising a proximal catheter hub permanently mounted to the elongate member, wherein the receptacle and cylindrical body are housed within the proximal catheter hub.

20. The catheter of claim 15, further comprising a distal ultrasonic transducer mounted to the catheter drive shaft.

21. The catheter of claim 1 wherein the engagement between the driven and driver members is controlled with hysteresis to prevent the driven and driver members from re-engaging each other until the applied torque falls substantially below the critical magnitude.

22. The catheter of claim 6 wherein the engagement between the driven and driver members is controlled with hysteresis to prevent the driven and driver members from re-engaging each other until the applied torque falls substantially below the critical magnitude.

23. The catheter of claim 15 wherein the engagement between the driven and driver members is controlled with hysteresis to prevent the driven and driver members from re-engaging each other until the applied torque falls substantially below the critical magnitude.

* * * * *